(12) United States Patent
Caborn et al.

(10) Patent No.: US 8,828,052 B2
(45) Date of Patent: Sep. 9, 2014

(54) METHOD AND APPARATUS FOR MENISCAL REPAIR

(75) Inventors: David Caborn, Goshen, KY (US);
Dennis McDevitt, Raleigh, NC (US);
Akbar Nawab, Louisville, KY (US);
Vincent Novak, Longmont, CO (US)

(73) Assignee: Linvatec Corporation, Largo, FL (US)

( * ) Notice: Subject to any disclaimer, the term of this patent is extended or adjusted under 35 U.S.C. 154(b) by 344 days.

(21) Appl. No.: 12/417,571

(22) Filed: Apr. 2, 2009

(65) Prior Publication Data

US 2010/0049212 A1   Feb. 25, 2010

Related U.S. Application Data

(60) Provisional application No. 61/072,683, filed on Apr. 2, 2008, provisional application No. 61/135,149, filed on Jul. 17, 2008, provisional application No. 61/208,294, filed on Feb. 23, 2009.

(51) Int. Cl.
*A61B 17/04* (2006.01)

(52) U.S. Cl.
CPC ..... *A61B 17/0401* (2013.01); *A61B 2017/0417* (2013.01); *A61B 2017/0456* (2013.01); *A61B 2017/0427* (2013.01); *A61B 2017/0409* (2013.01)
USPC ........................................ 606/232

(58) Field of Classification Search
USPC .............. 606/139, 228, 232, 144, 141
See application file for complete search history.

(56) References Cited

U.S. PATENT DOCUMENTS

| | | | |
|---|---|---|---|
| 3,209,422 A | 10/1965 | Dritz | |
| 3,399,432 A | 9/1968 | Merser | |
| 3,527,223 A | 9/1970 | Shein | |
| 3,716,058 A | 2/1973 | Tanner, Jr. | |
| 3,931,667 A | 1/1976 | Merser et al. | |
| 3,990,619 A | 11/1976 | Russell | |
| 4,006,747 A | 2/1977 | Kronenthal et al. | |
| 4,235,238 A | 11/1980 | Ogiu et al. | |
| 4,586,502 A | 5/1986 | Bedi et al. | |
| 4,635,637 A | 1/1987 | Schreiber | |
| 4,649,952 A | 3/1987 | Jobe | |
| 4,669,473 A | 6/1987 | Richards et al. | |
| 4,736,746 A | 4/1988 | Anderson | |
| 4,741,330 A | 5/1988 | Hayhurst | |
| 4,823,794 A * | 4/1989 | Pierce | 606/232 |
| 4,898,156 A | 2/1990 | Gatturna et al. | |
| 4,899,743 A | 2/1990 | Nicholson et al. | |
| 5,041,129 A | 8/1991 | Hayhurst et al. | |

(Continued)

FOREIGN PATENT DOCUMENTS

WO      WO 01/39671 A1     6/2001
WO      WO 02/36020        5/2002

(Continued)

*Primary Examiner* — Katherine M Shi
(74) *Attorney, Agent, or Firm* — Pandiscio & Pandiscio

(57) ABSTRACT

An anchor for securing suture to tissue, the anchor comprising:
an elongated body having a distal end and a proximal end, the distal end having a distal slot extending proximally into the elongated body, and the proximal end having a proximal slot extending distally into the body;
the distal slot comprising a wide section and a narrow section, wherein the wide section has a width such that the suture is slidably accommodated therein and the narrow section has a width such that the suture is bound therein, and further wherein the wide section is disposed distally of the narrow section.

22 Claims, 25 Drawing Sheets

(56) References Cited

U.S. PATENT DOCUMENTS

| | | | |
|---|---|---|---|
| 5,269,809 A | 12/1993 | Hayhurst et al. | |
| 5,320,633 A | 6/1994 | Allen et al. | |
| 5,417,691 A | 5/1995 | Hayhurst | |
| 5,464,426 A | 11/1995 | Bonutti | |
| 5,522,846 A | 6/1996 | Bonutti | |
| 5,527,343 A | 6/1996 | Bonutti | |
| 5,549,631 A | 8/1996 | Bonutti | |
| 5,569,305 A | 10/1996 | Bonutti | |
| 5,584,862 A | 12/1996 | Bonutti | |
| 5,601,557 A | 2/1997 | Hayhurst | |
| 5,601,571 A | 2/1997 | Moss | |
| 5,647,874 A | 7/1997 | Hayhurst | |
| 5,718,717 A | 2/1998 | Bonutti | |
| 5,733,306 A | 3/1998 | Bonutti | |
| 5,782,862 A | 7/1998 | Bonutti | |
| 5,827,298 A | 10/1998 | Hart et al. | |
| 5,928,252 A | 7/1999 | Steadman et al. | |
| 5,941,439 A * | 8/1999 | Kammerer et al. | 227/67 |
| 6,033,430 A | 3/2000 | Bonutti | |
| 6,056,772 A | 5/2000 | Bonutti | |
| 6,066,160 A | 5/2000 | Colvin et al. | |
| RE36,974 E * | 11/2000 | Bonutti | 606/232 |
| 6,312,448 B1 | 11/2001 | Bonutti | |
| 6,500,195 B2 | 12/2002 | Bonutti | |
| 6,506,197 B1 * | 1/2003 | Rollero et al. | 606/148 |
| 6,508,830 B2 | 1/2003 | Steiner | |
| 6,524,317 B1 | 2/2003 | Ritchart et al. | |
| 6,635,073 B2 | 10/2003 | Bonutti | |
| 6,656,182 B1 | 12/2003 | Hayhurst | |
| 7,087,073 B2 | 8/2006 | Bonutti | |
| 7,153,312 B1 | 12/2006 | Torrie et al. | |
| 7,390,329 B2 | 6/2008 | Westra et al. | |
| 2002/0019649 A1 | 2/2002 | Sikora et al. | |
| 2002/0161401 A1 | 10/2002 | Steiner | |
| 2003/0130694 A1 | 7/2003 | Bojarski et al. | |
| 2004/0116963 A1 * | 6/2004 | Lattouf | 606/224 |
| 2004/0172046 A1 * | 9/2004 | Hlavka et al. | 606/142 |
| 2004/0243180 A1 * | 12/2004 | Donnelly et al. | 606/232 |
| 2005/0033363 A1 | 2/2005 | Bojarski et al. | |
| 2005/0080455 A1 | 4/2005 | Schmieding et al. | |
| 2005/0251210 A1 * | 11/2005 | Westra et al. | 606/232 |
| 2005/0283192 A1 * | 12/2005 | Torrie et al. | 606/228 |
| 2006/0100627 A1 | 5/2006 | Stone et al. | |
| 2006/0189993 A1 | 8/2006 | Stone | |
| 2006/0247642 A1 | 11/2006 | Stone et al. | |
| 2006/0265009 A1 | 11/2006 | Bonutti | |
| 2006/0282085 A1 | 12/2006 | Stone et al. | |
| 2007/0185532 A1 | 8/2007 | Stone et al. | |
| 2007/0195532 A1 | 8/2007 | Reisenauer et al. | |
| 2008/0027446 A1 | 1/2008 | Stone et al. | |
| 2008/0065114 A1 | 3/2008 | Stone et al. | |
| 2008/0091219 A1 | 4/2008 | Marshall et al. | |
| 2009/0088797 A1 | 4/2009 | Crombie et al. | |
| 2010/0036395 A1 * | 2/2010 | Miller | 606/139 |
| 2011/0071549 A1 | 3/2011 | Caborn et al. | |

FOREIGN PATENT DOCUMENTS

| | | |
|---|---|---|
| WO | WO 2004/037094 | 5/2004 |
| WO | WO 2007/111986 | 10/2007 |
| WO | WO 2007/139785 | 12/2007 |
| WO | WO 2009/124215 | 10/2009 |

* cited by examiner

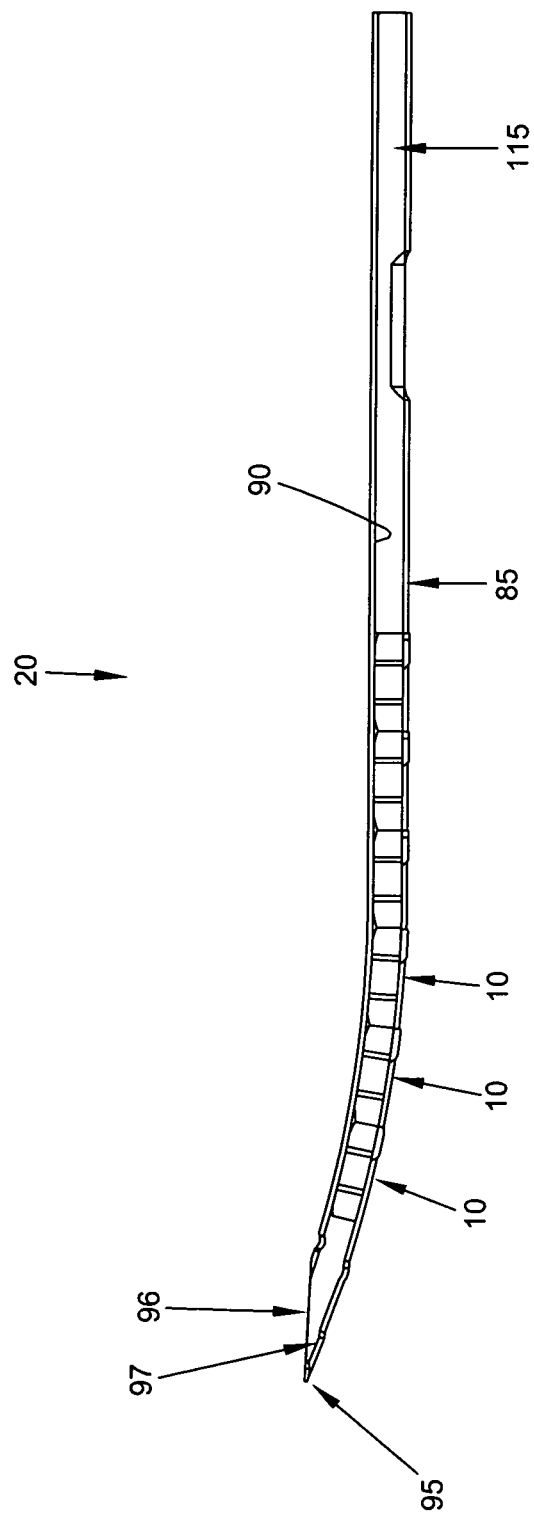

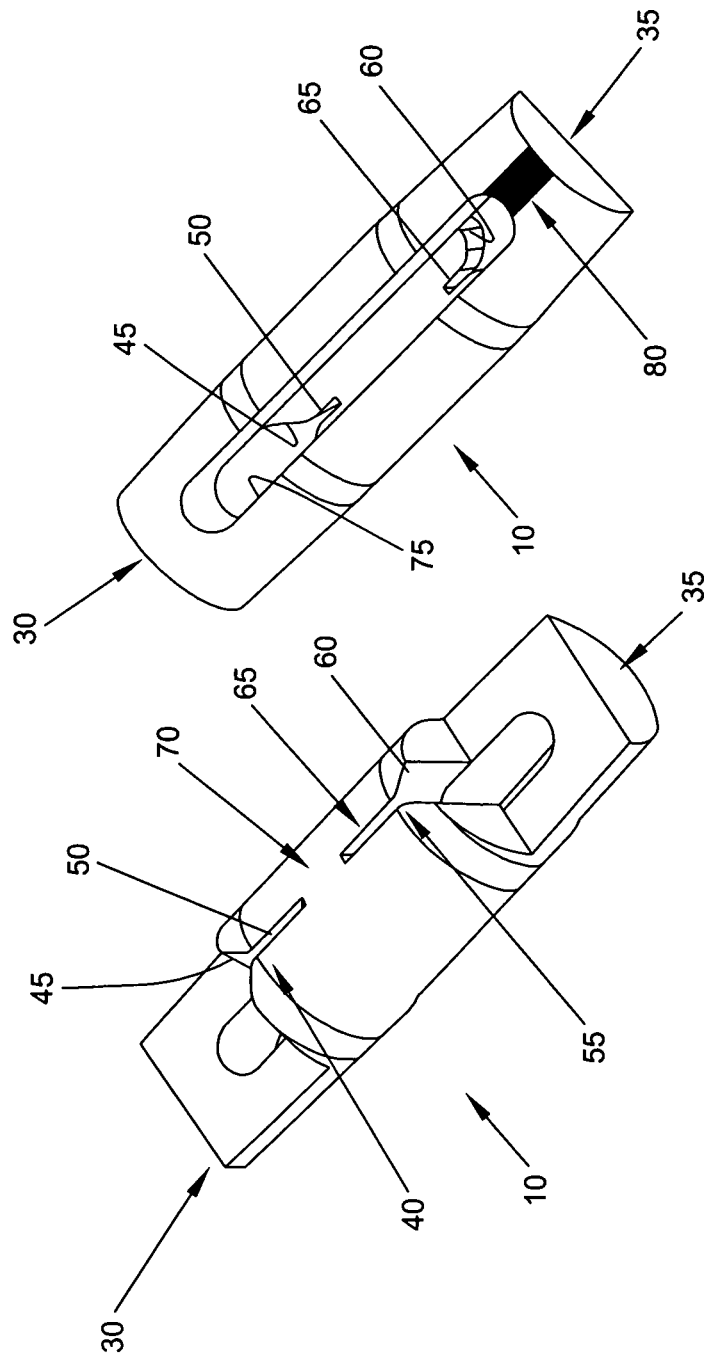

METHOD AND APPARATUS FOR MENISCAL REPAIR

This patent application claims benefit of:

(i) prior U.S. Provisional Patent Application Ser. No. 61/072,683, filed Apr. 2, 2008 by David Caborn et al. for MENISCAL REPAIR MAGAZINE CONCEPT;

(ii) prior U.S. Provisional Patent Application Ser. No. 61/135,149, filed Jul. 17, 2008 by David Caborn et al. for MENISCAL REPAIR PROVISIONAL 3; and (iii) prior U.S. Provisional Patent Application Ser. No. 61/208,294, filed Feb. 23, 2009 by Vincent Novak et al. for MENISCAL REPAIR PROVISIONAL 4.

The three above-identified patent applications are hereby incorporated herein by reference.

FIELD OF THE INVENTION

This invention relates to surgical methods and apparatus in general, and more particularly to surgical methods and apparatus for the repair of the meniscus.

BACKGROUND OF THE INVENTION

The meniscus is a piece of cartilage located within the knee joint, between the top of the tibia and the bottom of the femur. The meniscus serves to facilitate stable movement of the tibia and femur relative to one another, and to absorb shock and to spread load.

The meniscus is frequently damaged (e.g., torn) as the result of injury and/or accident. A damaged meniscus can impede proper motion of the knee joint and cause pain, among other problems.

More particularly, the essential role of an intact meniscus, and its importance for proper knee function, has been well documented and accepted by the general orthopedic community. An intact and functioning meniscus is critical to optimally distribute weightbearing forces that transfer through the knee joint while maintaining knee stability. The meniscus is also vital to preserving the articular cartilage surfaces of the knee. Loss of meniscal tissue is considered to be a key precursor to the development of knee osteoarthritis.

A major challenge in repairing a torn meniscus is the fact that the tissue itself is a fibrous structure that is not uniformly vascular. The vascular zones of the meniscus comprise about one third of the meniscus tissue and are generally recognized as the "red-red" and "red-white" zones. The red-red zone (i.e., the most highly vascularized portion of the meniscus) is an area in which meniscal repairs are known to heal easily and is located along its outer periphery. The red-white zone extends from the most vascular area towards the inner portions of the meniscus where the blood supply eventually declines to non-vascular tissue (which is sometimes referred to as the "white-white" zone). It is believed that proper surgical technique is of great importance if a successful repair is to be achieved in the red-white zone. It is generally accepted knowledge that about 15% of all meniscal tears occur in the red-red zone, another 15% of meniscal tears occur in the red-white zone, and the remaining 70% of meniscal tears occur in the white-white (or non-vascularized) zone of the meniscus.

Another significant challenge in repairing a torn meniscus is that the size and shape of the tears vary, making the reduction and apposition of the torn tissue difficult to accomplish. Without proper apposition and stability, torn meniscal tissue will not heal properly.

The art of repairing torn meniscal tissue was first developed and pioneered throughout the 1980's by early sports medicine-focused surgeons. The earliest methods employed only suture in the repair. The techniques of "inside-out" and "outside-in" suturing became the so-called "gold standard" for the repair of meniscal tissue. Both of these techniques focused on passing small diameter suture (size 2-0 or 3-0) through the meniscus, reducing and closing the tear, and then tying a suture knot over the knee capsule so as to fixate and stabilize the tear. A feature of these early all-suture repairs was that the surface of the meniscus was kept relatively smooth since the suture knot was outside of the knee joint, and the use of a needle and suture allowed the surgeon a great deal of flexibility in adequately reducing and stabilizing the tear. Eventually, these early surgeons began concomitant use of complementary techniques to promote a vascular response in the more non-vascular areas of the meniscus. Methods such as tear edge and meniscapsular rasping, the application of an interpositional blood clot, trephination to create a vascular channel, and fascial sheath or synovial flap coverage have been shown in several studies to be 150% more effective in healing a torn meniscus when compared to repairs that do not use such concomitant techniques.

The specific issues and challenges associated with the aforementioned all-suture inside-out and outside-in repair techniques are centered primarily on issues relating to the "user interface" and to the "tethering" of the meniscus to the knee capsule. More particularly, the "user interface" issues generally relate to the technical demands required in the operating room: the skill of the surgeon and the number of assistants required to safely pass the needle and suture from the anterior portion of the meniscus through the posterior portion of the meniscus and exit out through the posterior/medial aspect of the knee joint (i.e., the so-called "inside-out" technique); or the passing of a needle and suture from the medial aspect of the exterior of the knee into the knee joint, through the meniscus, the retrieval and re-insertion back into the meniscus, and then passage back out through the capsule to the medial aspect of the knee (i.e., the so-called "outside-in" technique). The aforementioned tethering issues relate to more recent concerns about fixating suture over the knee capsule and thereby "tethering" the meniscus to the knee capsule, since evidence suggests that such tethering of the meniscus to the knee capsule may interfere with the normal biomechanics of the meniscus (e.g., load and force distribution, etc.).

As recognition of the importance of the meniscus grew in the late 1980's, new methods of meniscus repair were developed. These new methods focused on improving execution of the procedure in order to make it easier, simpler and faster to accomplish. The new gold standard approach became the so-called "all-inside" technique. The all-inside technique is intended to not violate the knee capsule or require any incisions on the posterior/medial aspects of the knee (i.e., such as is required with the inside-out and outside-in suturing techniques discussed above). With the all-inside technique, the entire repair—both approximation and fixation—is performed intra-articularly.

The first all-inside repair devices were tack-like implants that were inserted through a standard arthroscopic portal and then forcefully pushed through the meniscus, crossing through the tear, thereby closing and fixing the tear without the use of suture. These tack-like implants were formed out of biomaterials such as PLA, PLLA or PGA that were expected to biodegrade over time. However, these materials are quite hard when first inserted and, in use, were found to degrade or bioabsorb much more slowly than anticipated. Clinical use and follow-up have demonstrated the inherent risks associated with the use of tack-like implants within the knee joint, as numerous published studies have reported device failure which can lead to tear reformation, loose implants within the knee joint and articular cartilage damage. Furthermore, it can be challenging for the surgeon to adequately address various tear shapes and sizes using these tack-like implants.

As a result, attention has returned to suture-based repairs, with a new focus on performing a suture-based repair using an all-inside technique. There are several recent systems that seek to accomplish this goal. However, none of these systems have been found to be completely satisfactory.

Thus, there is a need for a new and improved method and apparatus for meniscal repair.

SUMMARY OF THE INVENTION

The present invention provides a new and improved method and apparatus for meniscal repair.

In one form of the present invention, there is provided an anchor for securing suture to tissue, the anchor comprising:

an elongated body having a distal end and a proximal end, the distal end having a distal slot extending proximally into the elongated body, and the proximal end having a proximal slot extending distally into the body;

the distal slot comprising a wide section and a narrow section, wherein the wide section has a width such that the suture is slidably accommodated therein and the narrow section has a width such that the suture is bound therein, and further wherein the wide section is disposed distally of the narrow section.

In another form of the present invention, there is provided a system comprising:

a suture;

at least one anchor, the anchor comprising:

an elongated body having a distal end and a proximal end, the distal end having a distal slot extending proximally into the elongated body, and the proximal end having a proximal slot extending distally into the body;

the distal slot comprising a wide section and a narrow section, wherein the wide section has a width such that the suture is slidably accommodated therein and the narrow section has a width such that the suture is bound therein, and further wherein the wide section is disposed distally of the narrow section;

wherein the suture is initially disposed within the wide section of the distal slot of the at least one anchor so that the suture is slidable relative to the at least one anchor.

In another form of the present invention, there is provided a method for securing a first element to a second element, the method comprising the steps of:

providing a system comprising:

a suture;

at least two anchors, each anchor comprising:

an elongated body having a distal end and a proximal end, the distal end having a distal slot extending proximally into the elongated body, and the proximal end having a proximal slot extending distally into the body;

the distal slot comprising a wide section and a narrow section, wherein the wide section has a width such that the suture is slidably accommodated therein and the narrow section has a width such that the suture is bound therein, and further wherein the wide section is disposed distally of the narrow section;

wherein the suture is initially disposed within the wide section of the distal slot of each of the at least two anchors so that the suture is slidable relative to the at least two anchors; and an inserter, the inserter comprising a hollow elongated shaft having a sharp point disposed eccentric to the longitudinal axis of the hollow elongated shaft, and further wherein the suture and the at least two anchors are disposed within the lumen of the hollow elongated shaft;

passing the inserter through the first object and the second object so that the sharp point of the inserter resides on the far side of the second object;

ejecting the first anchor on the far side of the second object;

tensioning the suture so that the suture is drawn into the narrow section of the distal slot of the first anchor, whereby to bind the suture to the first anchor;

withdrawing the inserter out of the first object and the second object;

moving the inserter laterally;

passing the inserter back through the first object and the second object so that the sharp point of the inserter resides on the far side of the second object;

ejecting the second anchor on the far side of the second object;

tensioning the suture, and withdrawing the inserter out of the first object and the second object, so that the suture is drawn into the narrow section of the distal slot of the second anchor, whereby to bind the suture to the second anchor.

In another form of the present invention, there is provided a system for securing suture to tissue, the system comprising:

an anchor, the anchor comprising:

an elongated body having a distal end and a proximal end, the distal end having a distal slot extending proximally into the elongated body;

the distal slot comprising a wide section and a narrow section, wherein the wide section has a width such that the suture is slidably accommodated therein and the narrow section has a width such that the suture is bound therein, and further wherein the wide section is disposed distally of the narrow section.

In another form of the present invention, there is provided a method for securing a first object to a second object, the method comprising the steps of:

passing a first anchor having a strand of suture slidably mounted thereto through the first object and the second object at a first location;

securing the strand of suture to the first anchor;

passing a second anchor having the strand of suture slidably mounted thereto through the first object and the second object at a second location; and securing the strand of suture to the second anchor under tension.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIGS. 3A and 3B are schematic views showing the distal end of the meniscal repair system shown in FIGS. 1-3;

FIGS. 23 and 24 are schematic views showing an alternative anchor formed in accordance with the present invention.

DETAILED DESCRIPTION OF THE INVENTION

Figure 1:
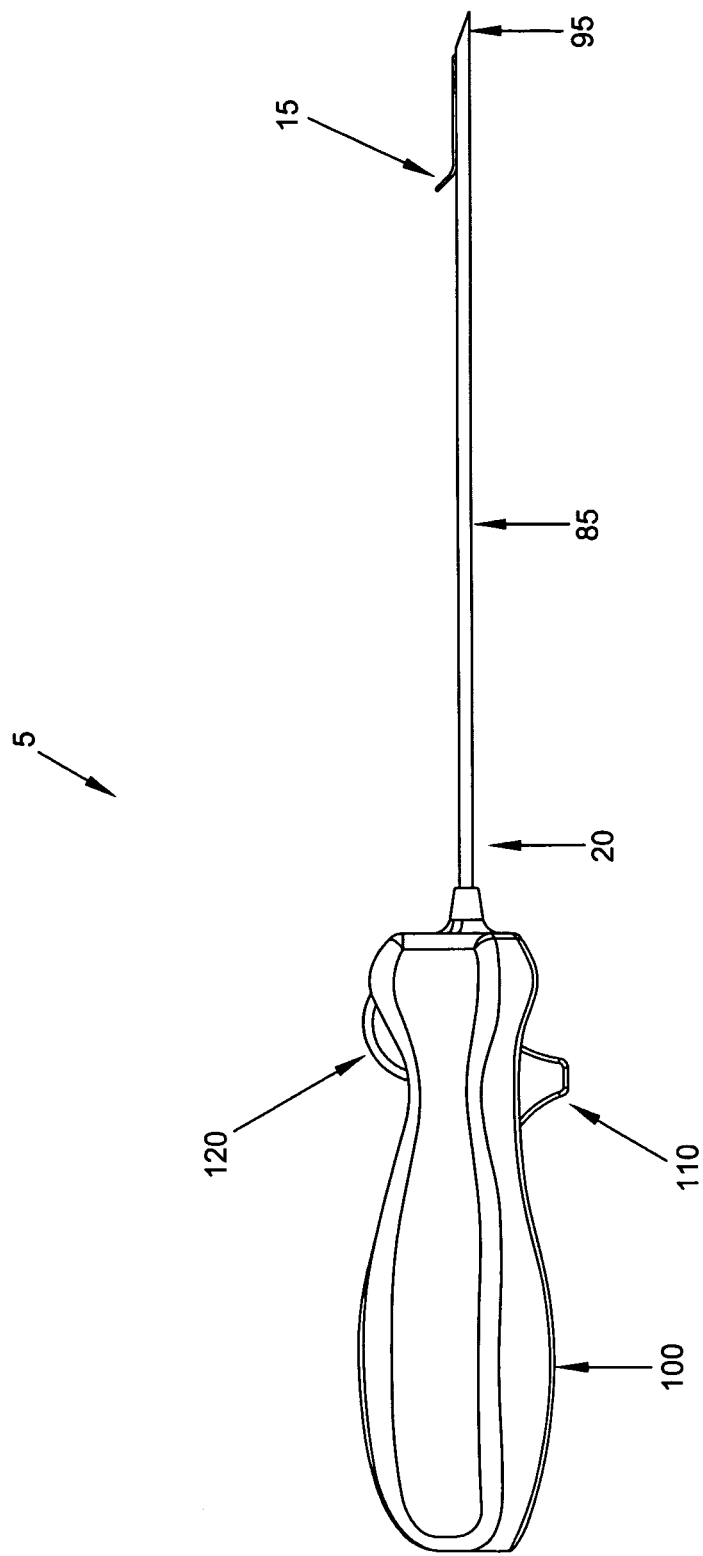
FIGS. 1-3 are schematic views showing a meniscal repair system formed in accordance with the present invention.
Figure 2:
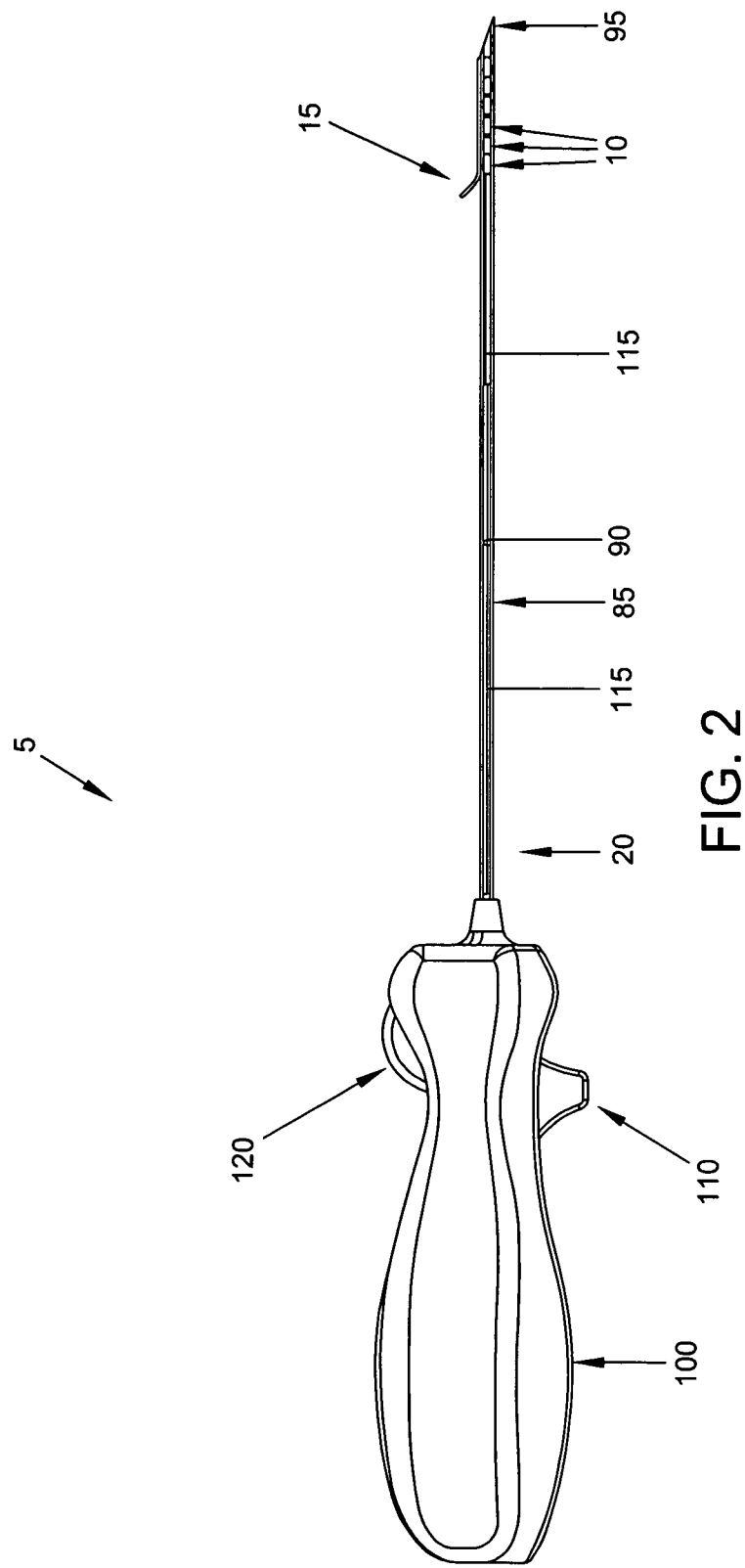
Figure 3:
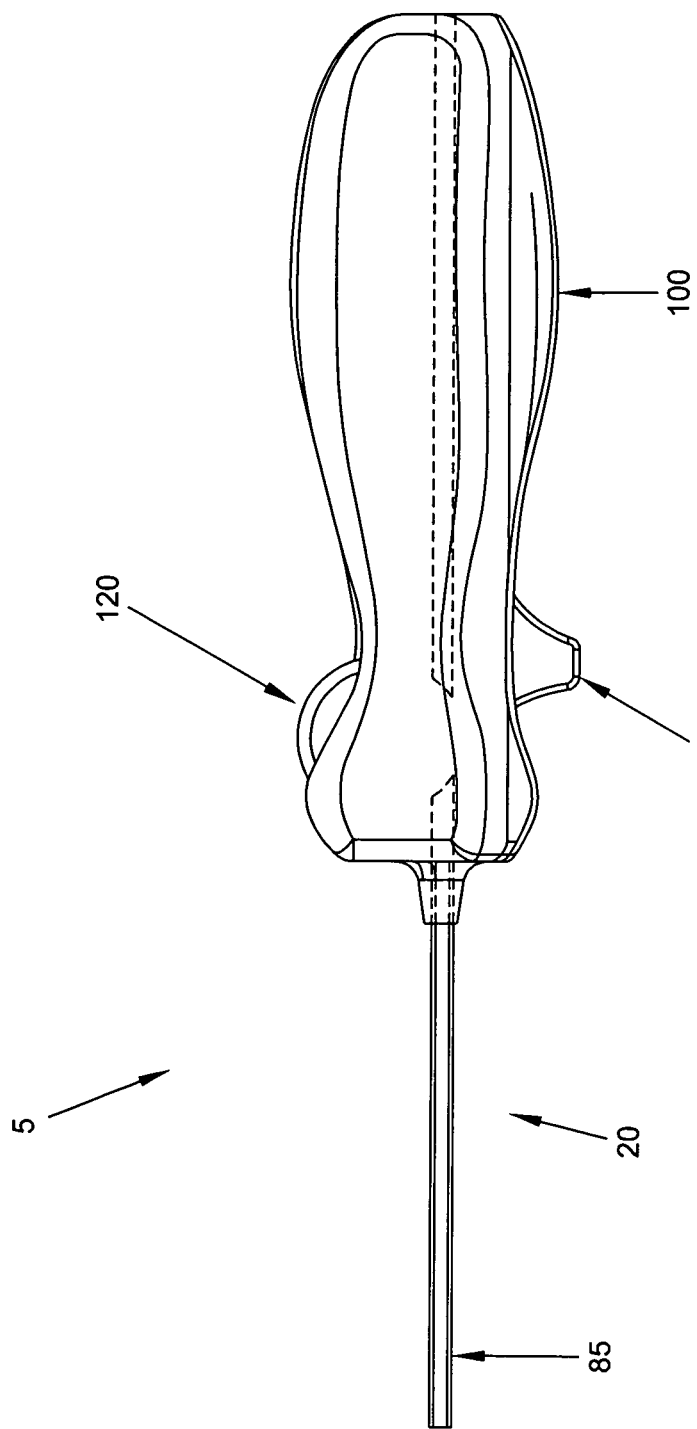
Figure 3B:
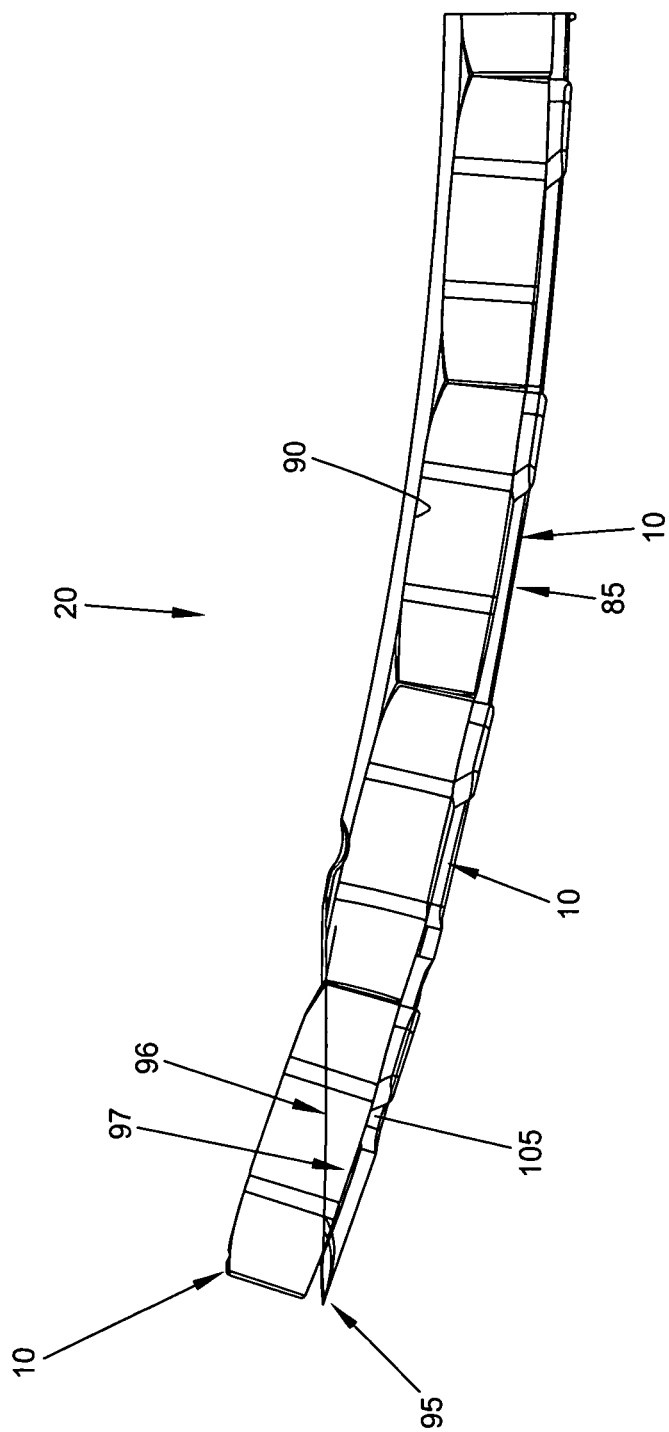
Figure 4:
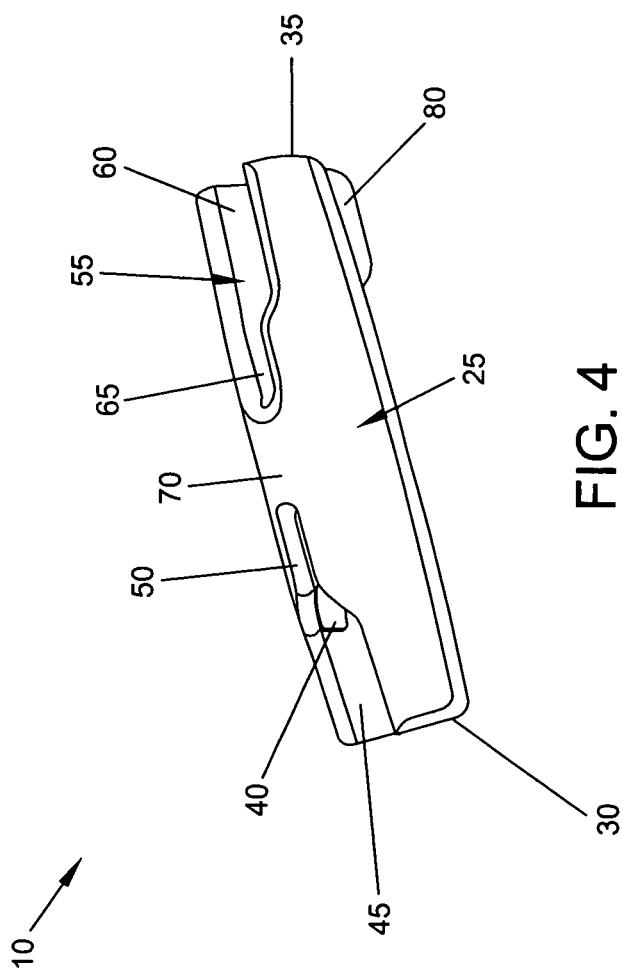
FIGS. 4-10 are schematic views showing further details of an anchor of the meniscal repair system shown in FIGS. 1-3.
Figure 5:
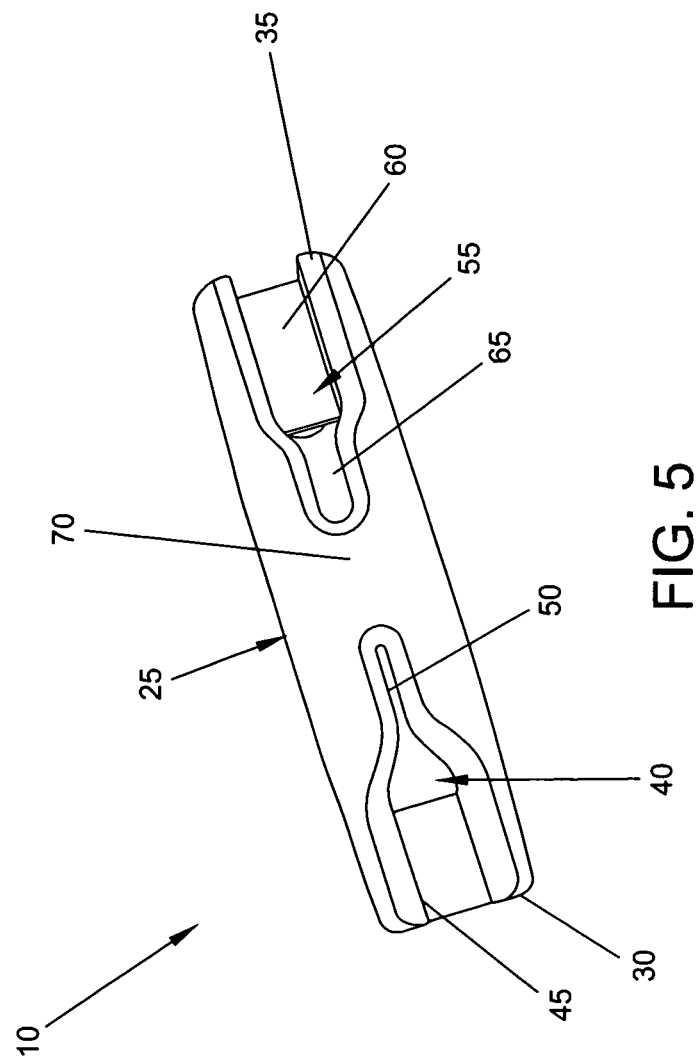
Figure 6:
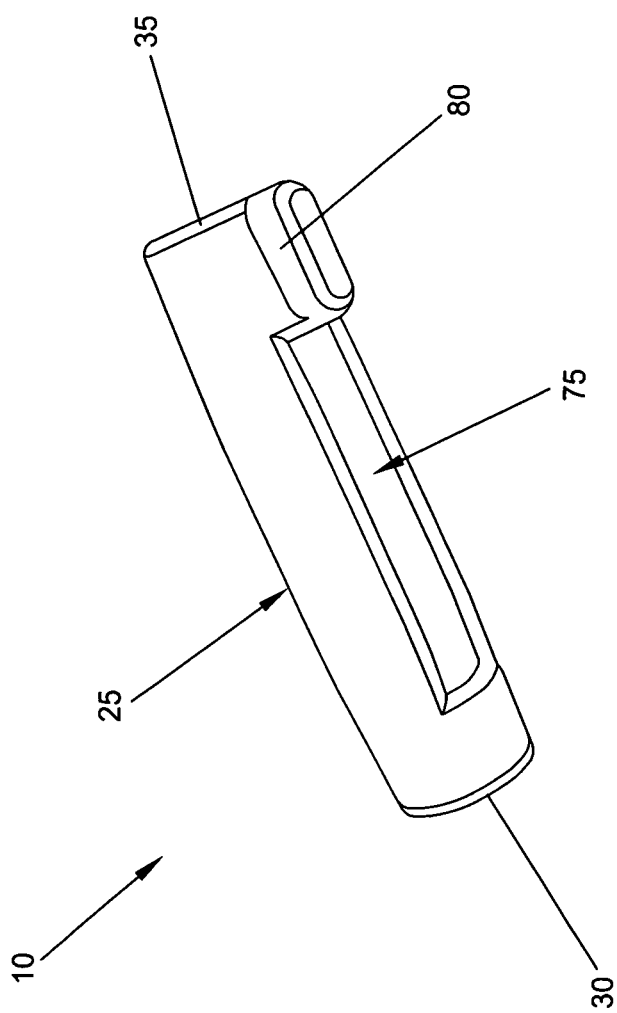

Looking first at FIGS. 1-3, 3A and 3B, there is shown a novel system 5 for meniscal repair. System 5 generally comprises a plurality of anchors 10, a length of suture 15 and an inserter 20.

Anchors 10 are shown in greater detail in FIGS. 4-10. Each of the anchors 10 generally comprises an elongated body 25 which, in its preferred construction, is generally cylindrical so that it can make a close sliding fit within the lumen of a hollow delivery needle, as will hereinafter be discussed in further detail. Elongated body 25 is characterized by a distal end 30 and a proximal end 35.

On a "top" side of elongated body 25, a distal slot 40 extends proximally along the elongated body, with distal slot 40 comprising a wide section 45 and a narrow section 50. Also on the "top" side of elongated body 25, a proximal slot 55 extends distally along the elongated body, with proximal slot 55 comprising a wide section 60 and a narrow section 65. Distal slot 40 is aligned with proximal slot 55. Preferably narrow section 50 of distal slot 40 is narrower than narrow section 65 of proximal slot 55 (FIG. 5), and preferably wide section 45 of distal slot 40 is the same width as wide section 60 of proximal slot 55. Thus it will be seen that narrow section 50 of distal slot 40 is narrower than narrow section 65, which is itself narrower than the wide section 45 of distal slot 40 and wide section 60 of proximal slot 55. Furthermore, the aforementioned narrow section 50, narrow section 65, wide section 45 and wide section 60 are sized relative to suture 15 so that: (i) suture 15 will make a tight binding fit with narrow section 50 of distal slot 40, (ii) suture 15 will make a sliding fit with narrow section 65 of proximal slot 55, and (iii) suture 15 will move easily through wide section 45 of distal slot 40 and wide section 60 of proximal slot 55. A wall 70 separates narrow section 50 of distal slot 40 from narrow section 65 of proximal slot 55.

Figure 7:
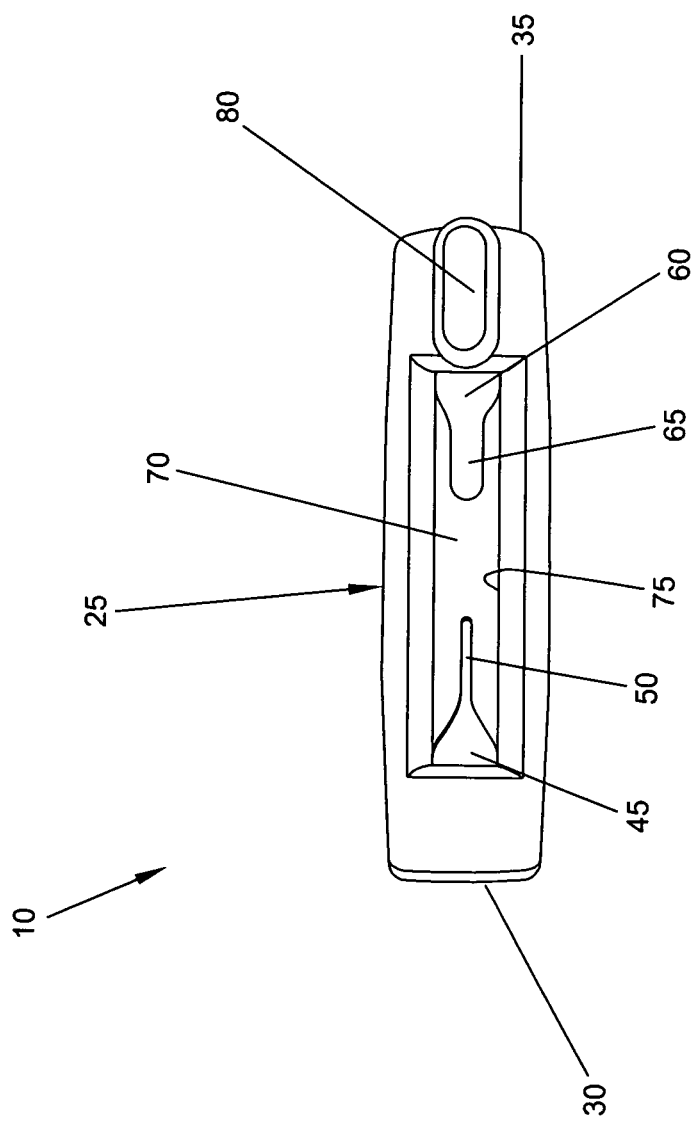
Figure 8:
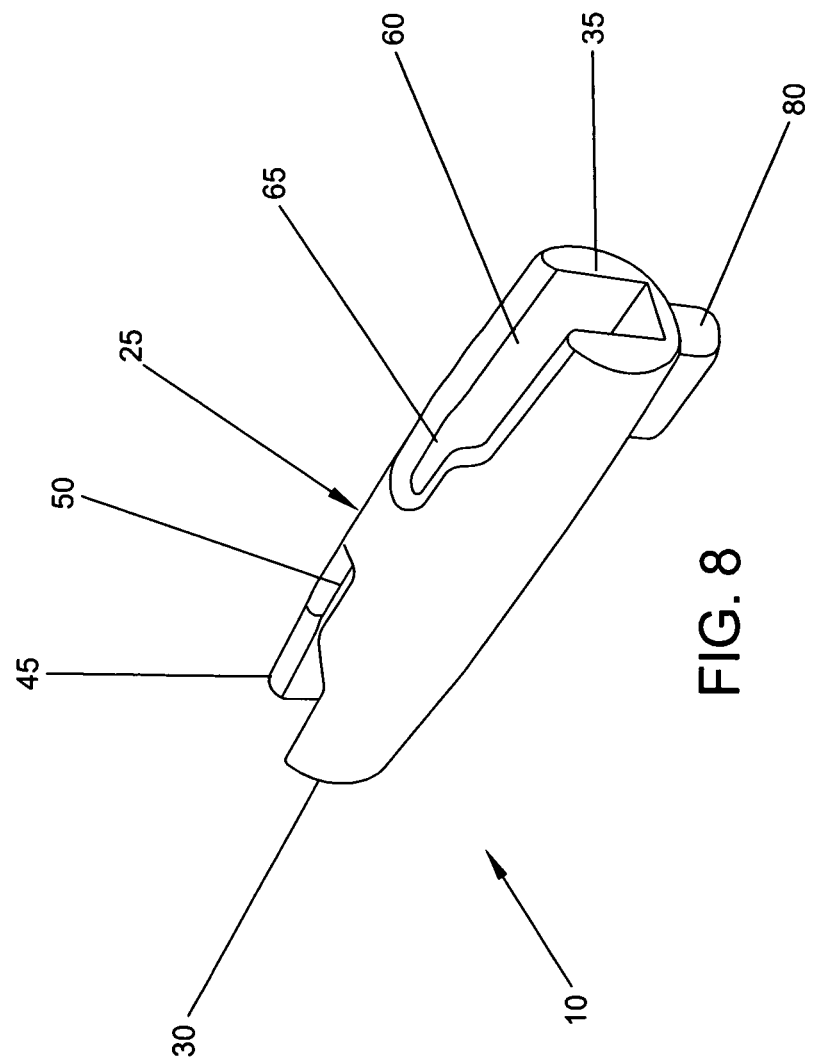
Figure 9:
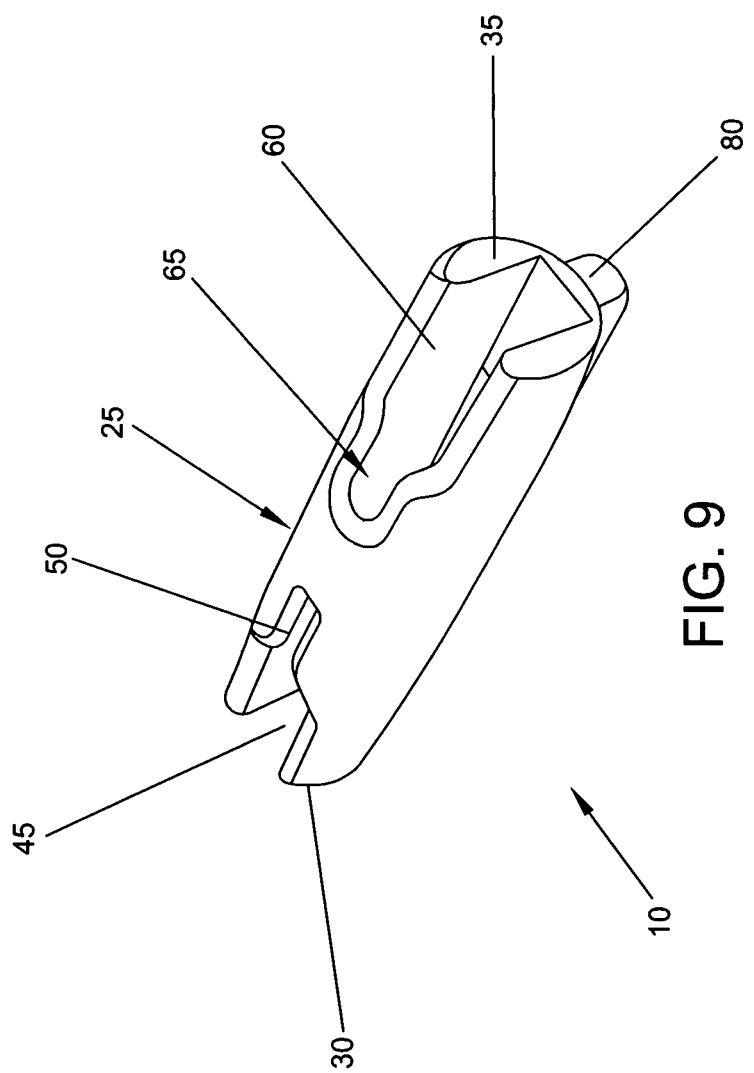
Figure 10:
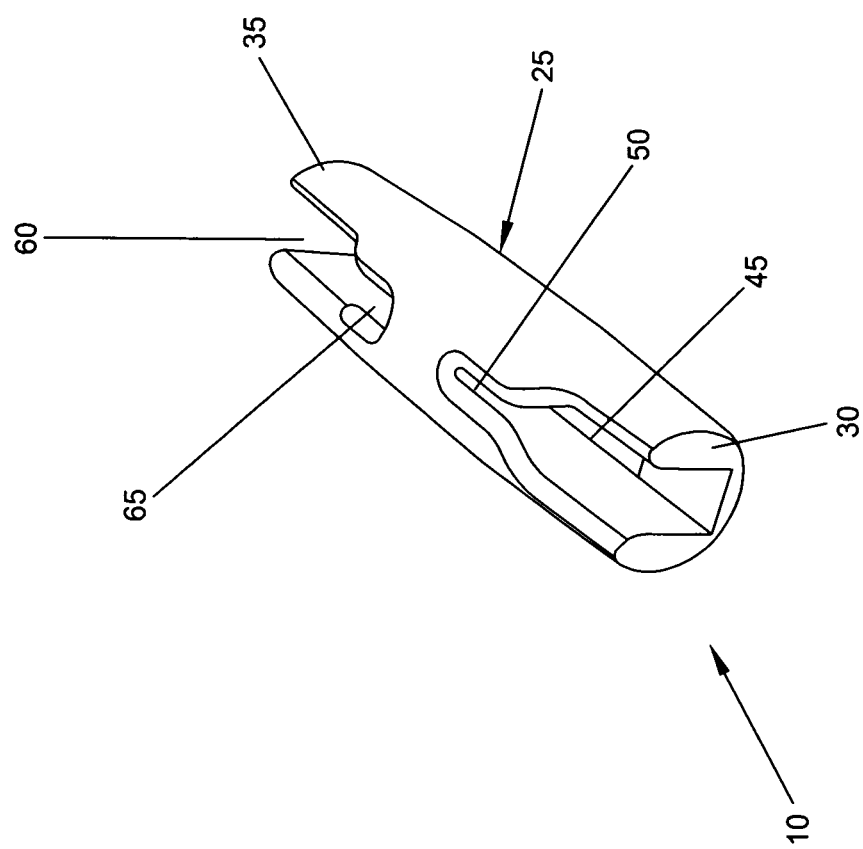

On a "bottom" side of elongated body 25 (i.e., on the side diametrically opposed to the aforementioned "top" side of elongated body 25), a recess 75 (FIGS. 6 and 7) extends into elongated body 25. Thus, recess 75 is diametrically opposed to the aforementioned distal slot 40 and proximal slot 55. Recess 75 is formed long enough, and deep enough, so that it communicates with narrow section 50 of distal slot 40 and with a portion of wide section 45 of distal slot 40, and it communicates with narrow section 65 of proximal slot 55 and with a portion of wide section 60 of proximal slot 55 (FIG. 7). Recess 75 is significantly wider than suture 15, so that suture 15 can move easily through recess 75.

On account of the foregoing construction, wide section 45 of distal slot 40, narrow section 50 of distal slot 40, recess 75, wide section 60 of proximal slot 55 and narrow section 65 of proximal slot 55 provide a suture pathway about elongated body 25 of anchor 10. Furthermore, and as will hereinafter be discussed in further detail, on account of the disposition and sizing of the aforementioned wide section 45, narrow section 50, recess 75, wide section 60 and narrow section 65, anchor 10 can be slidably mounted on the suture and then selectively secured to the suture.

A fin 80 extends "downwardly" out of the "bottom" side of elongated body 25. Fin 80 is aligned with recess 75 and diametrically opposed to distal slot 40 and proximal slot 55.

It should be appreciated that, while elongated body 25 is preferably generally cylindrical, it is also preferably not tubular: at no point along its length does elongated body 25 have a complete outer periphery with a hollow interior.

Suture 15 may comprise any suture material of the sort known in the art. By way of example but not limitation, suture 15 may comprise braided suture, so-called "monofilament" suture, etc., and may be formed so as to be either "permanent" or absorbable. In one preferred form of the invention, suture 15 comprises braided suture.

As will hereinafter be discussed in further detail, suture 15 is intended to be passed through anchor 10 (or, stated another way, anchor 10 is intended to be "strung" onto suture 15) by passing the suture through distal slot 40, into and along bottom recess 75, and back through proximal slot 55 (see FIGS. 14-16, 20, etc.). In this respect it will be appreciated that wide section 45 of distal slot 40, recess 75 and wide section 60 of proximal slot 55 are all sized sufficiently wide relative to suture 15 such that suture 15 can slide easily through those openings. Thus, so long as suture 15 remains disposed in those openings, suture 15 will be free to move easily through anchor 10 (and, correspondingly, anchor 10 will be free to slide easily along suture 15). However, and as will hereinafter be discussed in further detail, when suture 15 is directed into narrow section 50 of distal slot 40, a tight interference fit will be created between the anchor and the suture, thereby securing the anchor and suture to one another.

As will also hereinafter be discussed in further detail, a plurality of anchors 10 may be "strung" on a single suture 15 (see FIGS. 2, 13, 15, 20, etc.). As noted above, when suture 15 passes through wide section 45 of distal slot 40, recess 75 and wide section 60 of proximal slot 55 of each anchor 10, the anchors may be advanced along the suture. However, and as will hereinafter be discussed in further detail, when suture 15 is directed into narrow section 50 of distal slot 40 of an anchor, a tight interference fit will be created between that anchor and the suture, thereby securing that anchor and the suture to one another. Significantly, and as will hereinafter be discussed in further detail, when a plurality of anchors 10 are slidably mounted on a single suture 15, each of the anchors 10 may be selectively and individually secured to the suture when and where desired by the user.

Figure 12:
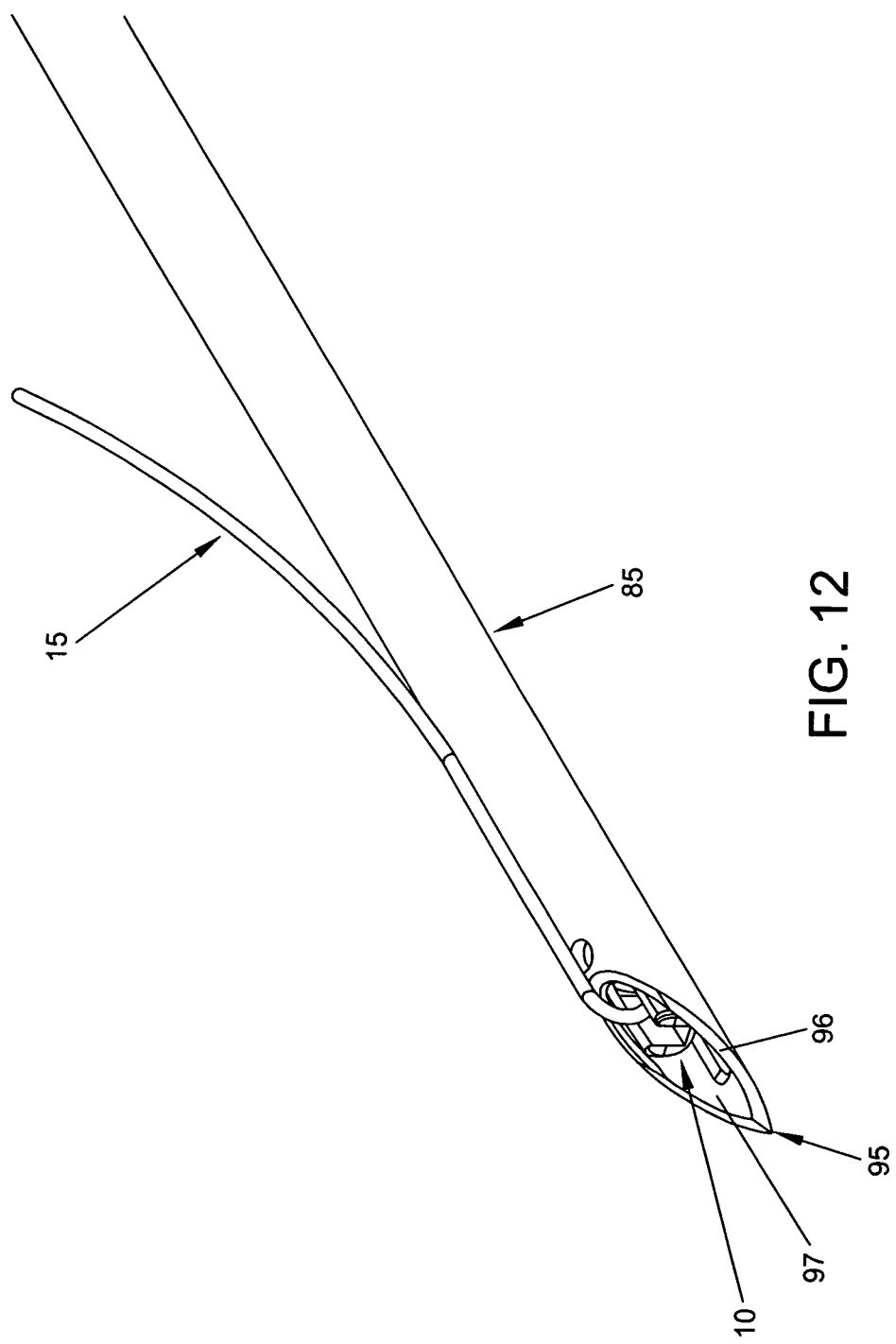
FIGS. 12-17 are schematic views showing an anchor being deployed from an inserter.
Figure 13:
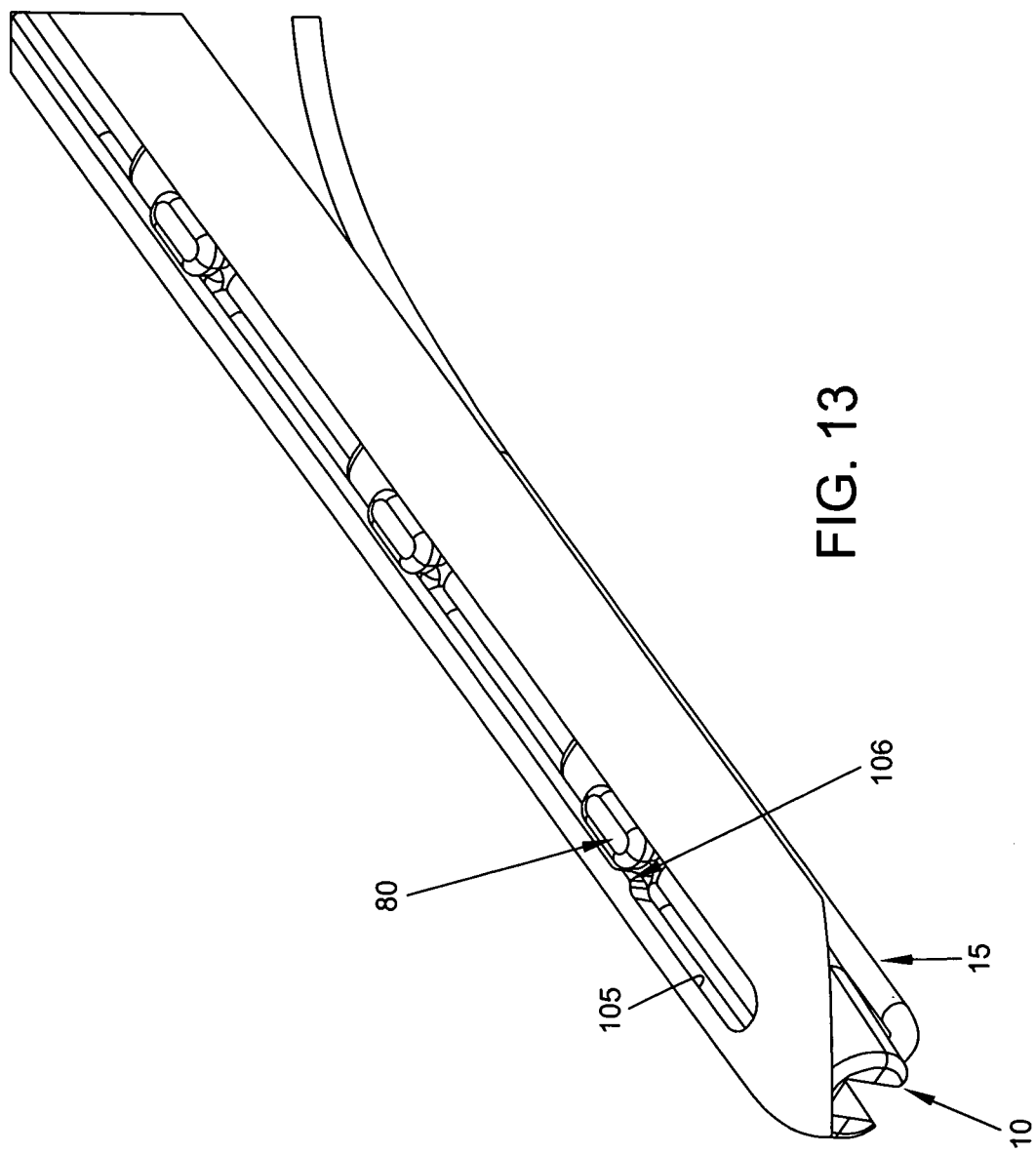
Figure 14:
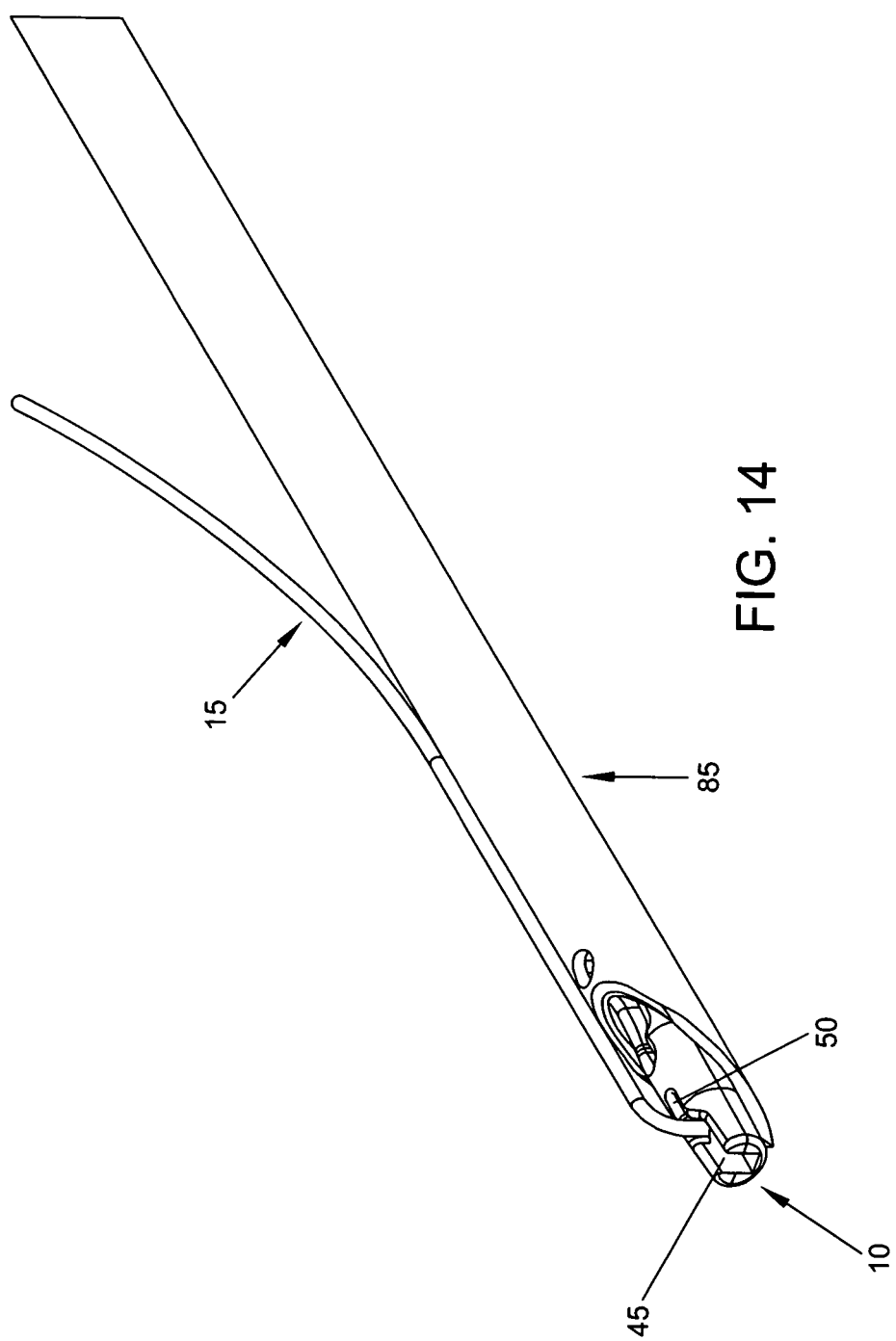
Figure 15:
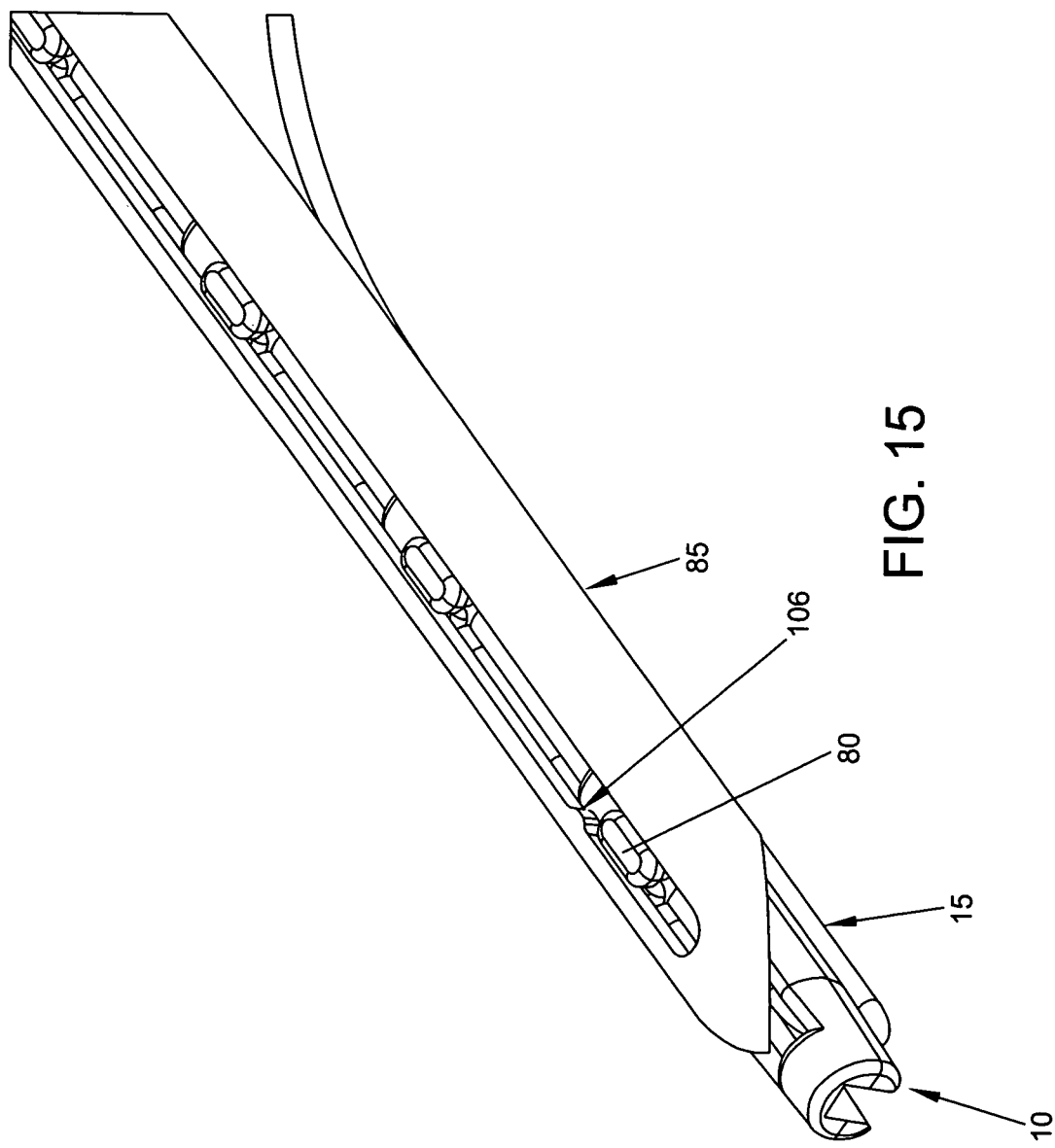
Figure 16:
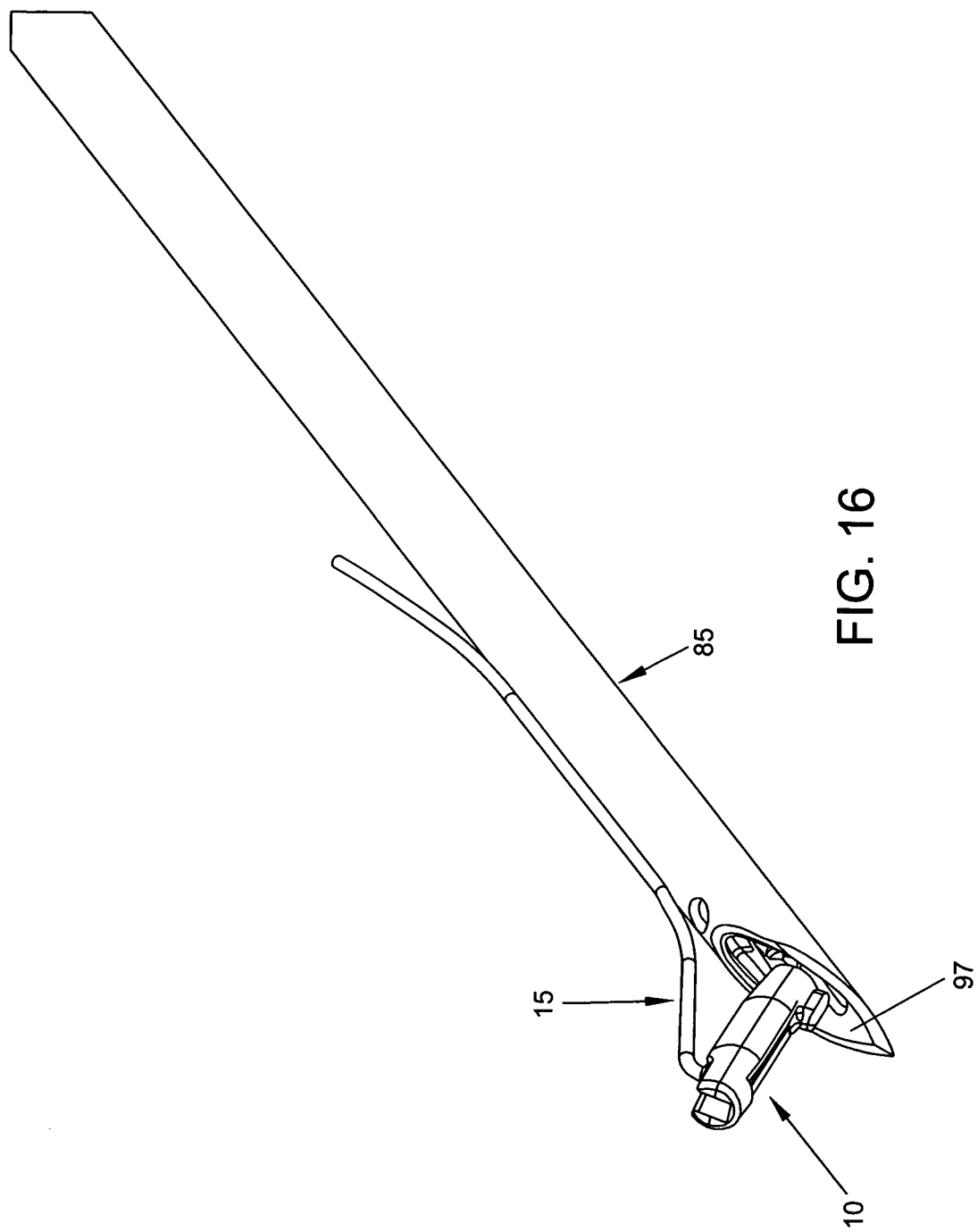
Figure 17:
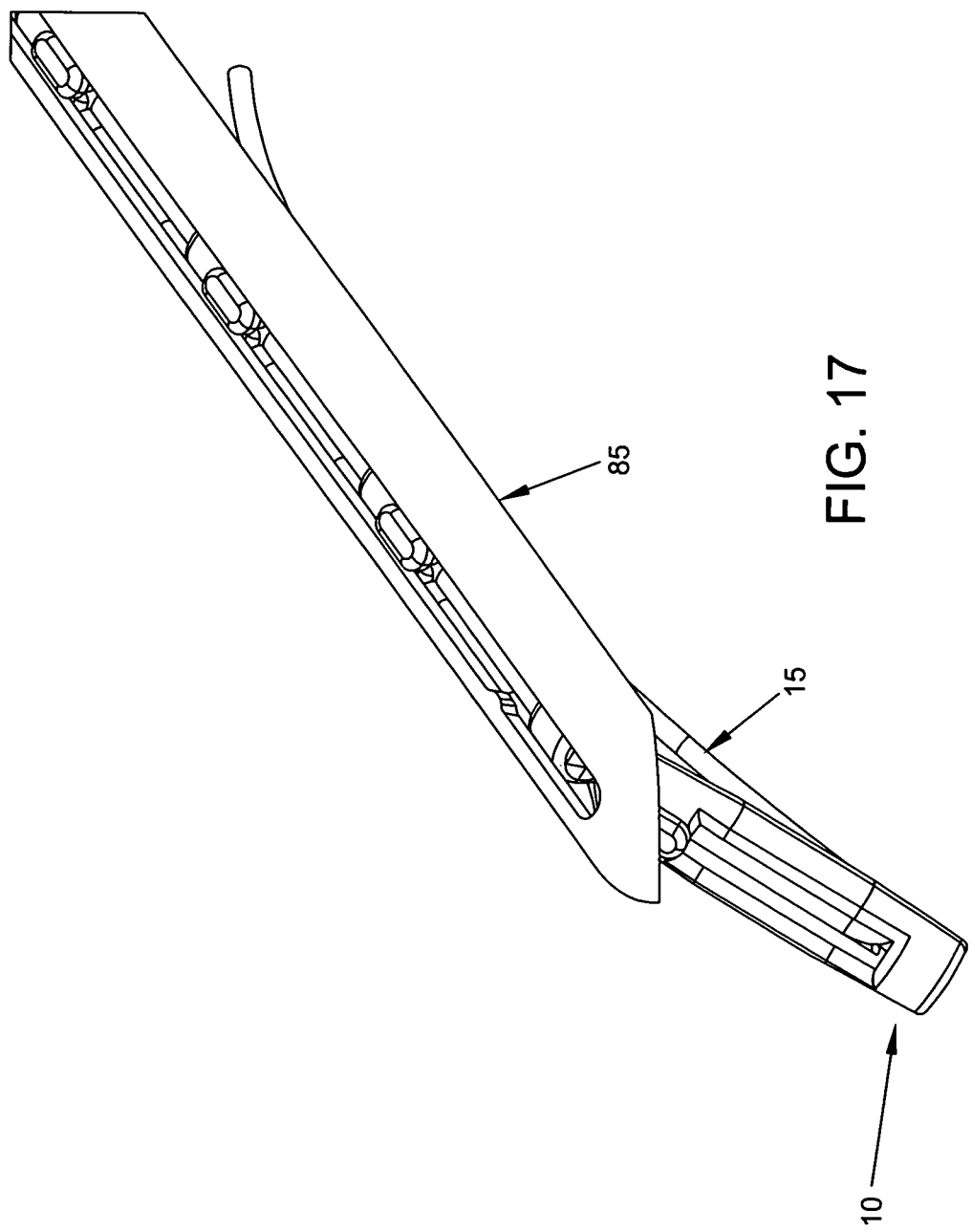

Looking again at FIGS. 1-3, 3A and 3B, inserter 20 generally comprises an elongated shaft 85 having a central lumen 90 extending therethrough. Elongated shaft 85 terminates in a sharp point 95 at its distal end. Sharp point 95 is created by forming an oblique face 96 (FIGS. 3A, 3B and 12) on the distal end of the elongated shaft, such that a section 97 of elongated shaft 85 is exposed at the mouth of lumen 90. A handle 100 (FIGS. 1-3) is secured to elongated shaft 85 at its proximal end. A slot 105 (FIG. 13) is formed in elongated shaft 85 on its "bottom" side. Slot 105 extends into exposed section 97 (FIGS. 12 and 13) of elongated shaft 85. A small projection 106 (FIGS. 13 and 15) extends into slot 105.

As seen in FIGS. 2, 3A, 3B and 13, elongated shaft 85 is sized to receive a plurality of anchors 10 therein, with those anchors being "strung" on a single suture 15. To this end, lumen 90 of elongated shaft 85 is sized to slidably receive elongated bodies 25 of anchors 10, with fins 80 extending out through slot 105 of elongated shaft 85. Fins 80 and slot 105 cooperate to keep anchors 10 aligned within lumen 90 of elongated shaft 85. The aforementioned small projection 106 provides nominal resistance to the passage of fins 80 through slot 105. Small projection 106 is positioned such that the lead anchor 10 in lumen 90 normally does not exit the distal end of the elongated shaft; however, with the application of a distally-directed force, fin 80 can slip past small projection 106 so as to release the lead anchor from lumen 90.

Preferably, handle 100 includes a lever 110 for selectively advancing a drive shaft 115 along lumen 90 of elongated shaft 85, whereby to selectively advance anchors 10 along lumen 90 and thereby eject anchors 10 one at a time from the distal end of elongated shaft 85. Handle 100 preferably also includes a tension wheel 120 for selectively tensioning the suture emerging from the proximal-most anchor 10 which is held in lumen 90 of elongated shaft 85. To this end, drive shaft 115 is preferably hollow so that suture 15 can extend from the proximal-most anchor 10, through the drive shaft and be engaged by tension wheel 120.

Figure 11:
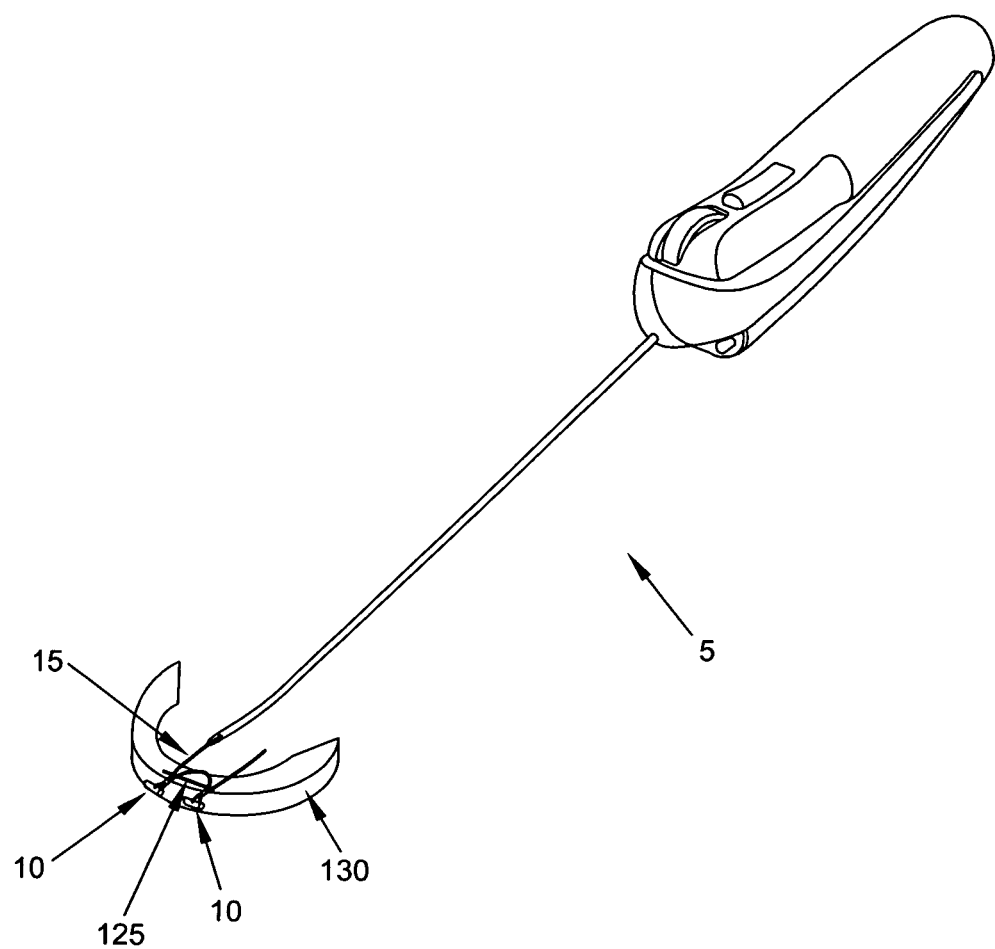
FIG. 11 is a schematic view showing a meniscal repair effected using the system shown in FIGS. 1-3.
Figure 18:
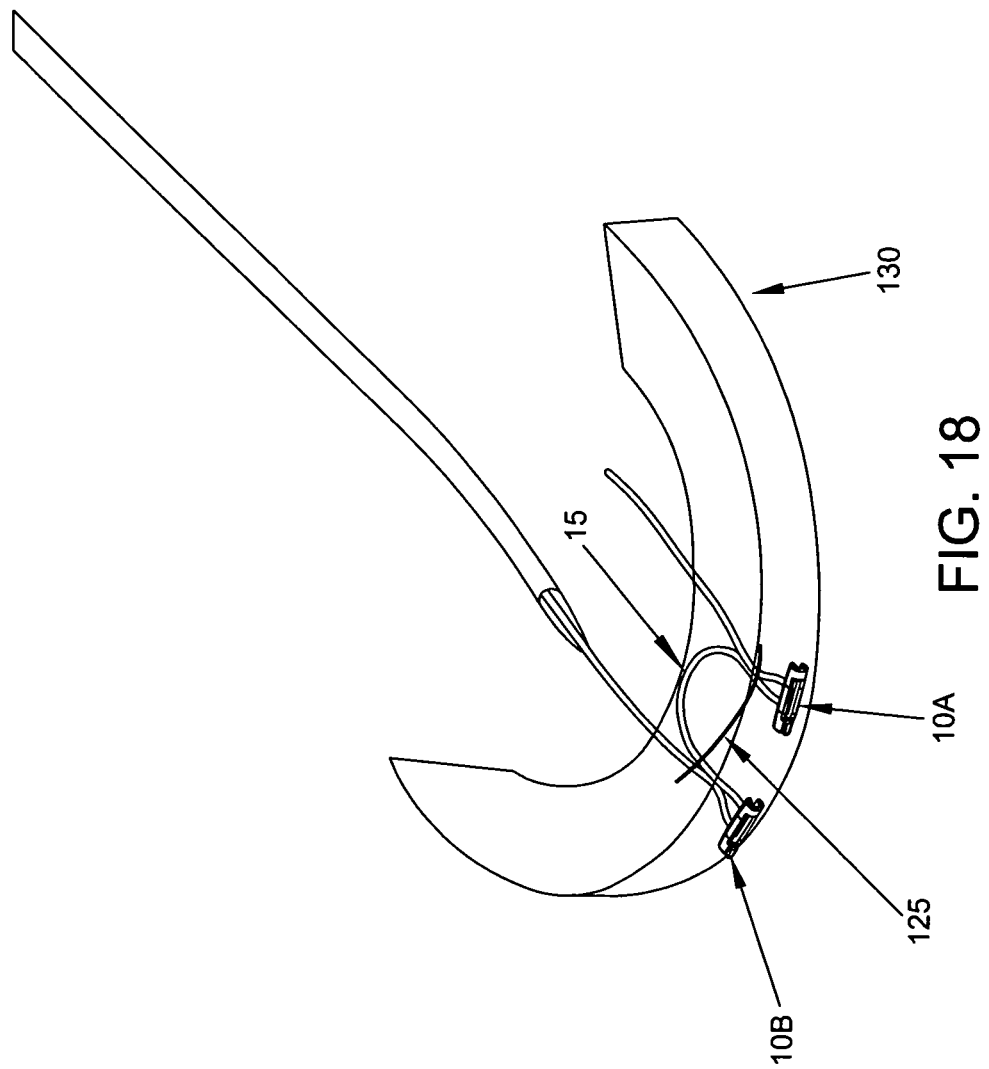
FIG. 18 is another schematic view showing a meniscal repair effected using the system shown in FIGS. 1-3.

As seen in FIG. 11, system 5 may be used to close a tear 125 in a meniscus 130 using a plurality of anchors 10 and a suture 15. More particularly, and looking now at FIGS. 11-18, sharp point 95 of inserter 20 is advanced into meniscus 130, across tear 125, and then out the far side of meniscus 130. Then the leading anchor 10 in lumen 90 (i.e., anchor 10A in FIG. 18) is ejected from elongated shaft 85. This is done by advancing drive shaft 115 (e.g., with lever 110) so that the leading anchor 10 has its fin 80 forced past small projection 106 in slot 105, whereby to release the anchor from the inserter. As the leading anchor 10 is ejected from lumen 90, suture 15 initially resides in wide section 45 of distal slot 40. However, by holding suture 15 under tension as anchor 10 is forced out of lumen 90 by drive shaft 115, anchor 10 is turned (i.e., away from exposed section 97 of elongated shaft 85) and suture 15 is forced into narrow section 50 of distal slot 40, whereby to secure suture 15 to anchor 10 in a cleating action. At the same time, another portion of suture 15 advances from wide section 60 of proximal slot 55 into narrow section 65 of proximal slot 55. Thus, at this point suture 15 will extend through narrow section 50 of distal slot 40, recess 75 and narrow section 65 of proximal slot 55, with the suture being secured to the anchor by virtue of the tight binding fit established between narrow section 50 of distal slot 40 and suture 15.

Then, while keeping suture 15 under tension so that anchor 10 remains positioned against the far side of meniscus 130, inserter 20 is withdrawn back across the meniscus, moved laterally by an appropriate distance, re-inserted across tear 125, passed out the far side of meniscus 130, and another anchor 10 (i.e., anchor 10B in FIG. 18) is deployed. Again, suture 15 is held under tension as the second anchor is deployed on the far side of the meniscus so that anchor 10 is turned (i.e., away from exposed section 97 of elongated shaft 85) and suture 15 is forced into the narrow section 50 of the distal slot 40 of that second anchor, whereby to secure that second anchor in a cleating action. Again, as this occurs, another portion of suture 15 advances from wide section 60 of proximal slot 55 into narrow section 65 of proximal slot 55. Thus, at this point suture 15 will extend through narrow section 50 of distal slot 40, recess 75 and narrow section 65 of proximal slot 55, with the suture being secured to the anchor by virtue of the tight binding fit established between narrow section 50 of distal slot 40 and suture 15.

Thus, the suture length extending between the first-deployed anchor (i.e., anchor 10A in FIG. 18) and the second-deployed anchor (i.e., anchor 10B in FIG. 18) is maintained under tension so as to hold tear 125 closed.

Figure 19:
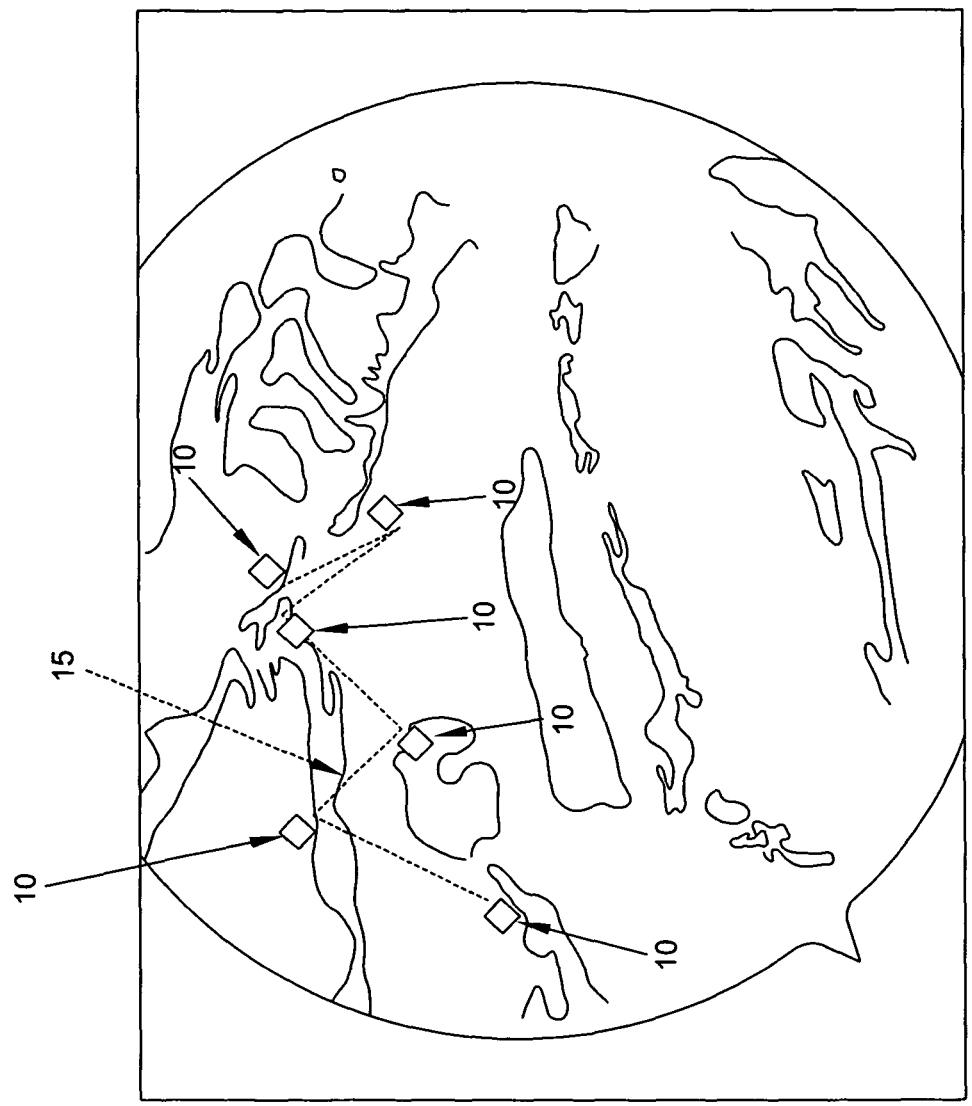
FIG. 19 is still another schematic view showing a meniscal repair effected using the system shown in FIGS. 1-3.
Figure 20:
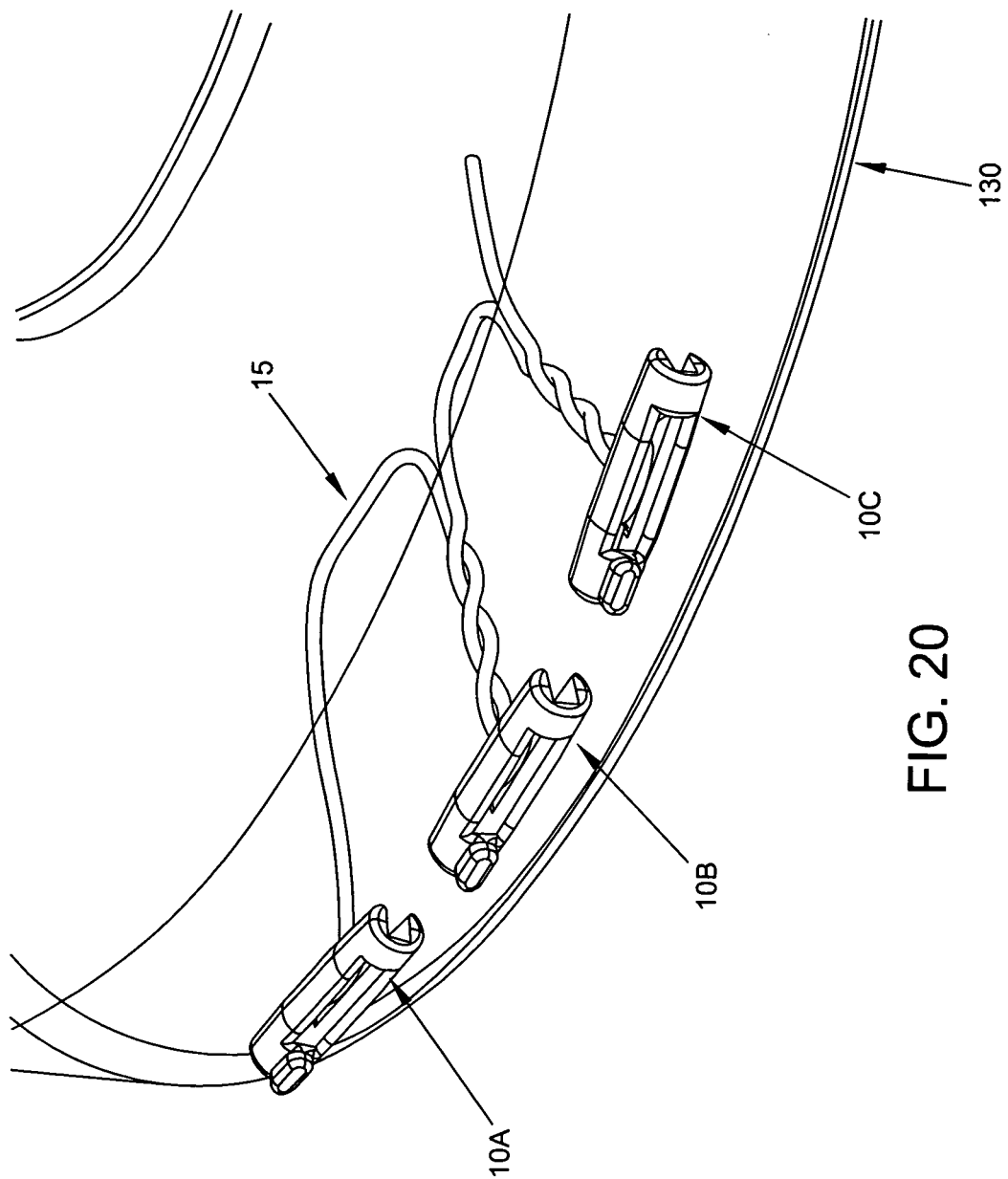
FIGS. 20-22 are schematic views showing how the suture may be twisted so as to enhance the holding strength of the meniscal repair system.

This operation may thereafter be repeated as many times as is necessary in order to close the tear. See, for example, FIG. 19, where six anchors 10, all connected by a single suture 15, are used to close a tear in the meniscus using a complex running stitch. This ability to set a variable number of anchors in the repair procedure, limited only by the number of anchors held in inserter 20, is a significant advance in the art.

If desired, a small knot may be formed in the suture after placement of the last anchor for added holding strength. However, it should be appreciated that this knotting step is purely optional and not required.

It will be appreciated that, since anchors 10 are turned away from exposed section 97 of elongated shaft 85 during deployment, the disposition of elongated shaft 85 can largely regulate the disposition of anchors 10 relative to the meniscus. Thus, where exposed section 97 of elongated shaft 85 is oriented so that it is in the "6 o'clock" or "12 o'clock" position, the anchor will be set against the meniscus with a vertical disposition. Correspondingly, where exposed section 97 of elongated shaft 85 is oriented so that it is in the "3 o'clock" or "9 o'clock" position, the anchor will be set with a horizontal disposition (e.g., in the manner shown in FIGS. 11 and 18). Of course, in some situations it may be possible to thereafter adjust the disposition of an anchor 10 against the meniscus, e.g., by using a grasper to manually turn the anchor.

In one preferred form of the invention, the first anchor 10 in inserter 20 may have suture 15 permanently secured thereto, e.g., prior to insertion of the inserter into the meniscus. By way of example but not limitation, suture 15 may be glued, welded or otherwise secured to first anchor 10. Furthermore, where suture 15 is so secured to first anchor 10, the terminated suture may terminate substantially within the anchor or it may extend out of the anchor, as desired.

Significantly, since suture 15 is secured to each deployed anchor, the failure of any one suture stitch does not threaten the integrity of the remainder of the repair. Indeed, if a suture stitch were to fail (e.g., break), it would not disrupt the intact stitches in the remainder of the repair. The removed anchor could then be replaced by two or more additional anchors so as to reinforce the repair.

It will be appreciated that the holding power of each anchor 10 on suture 15 is a function of the cleating action provided by that anchor on suture 15. It will also be appreciated that this cleating action is largely a function of the binding interference fit which is established between the suture and narrow section 50 of distal slot 40, since the suture makes a loose fit through recess 75 and a sliding fit with narrow section 65 of proximal slot 55. In practice, it has been found that approximately 35 Newtons of holding strength can be provided without reducing the width of narrow section 50 of distal slot 40 to the point where it becomes excessively difficult to insert the suture into narrow section 50 and/or where the act of insertion causes damage to the suture. In the great majority of cases, a holding strength of approximately 35 Newtons has been found to be more than adequate for meniscal repair.

Figure 21:
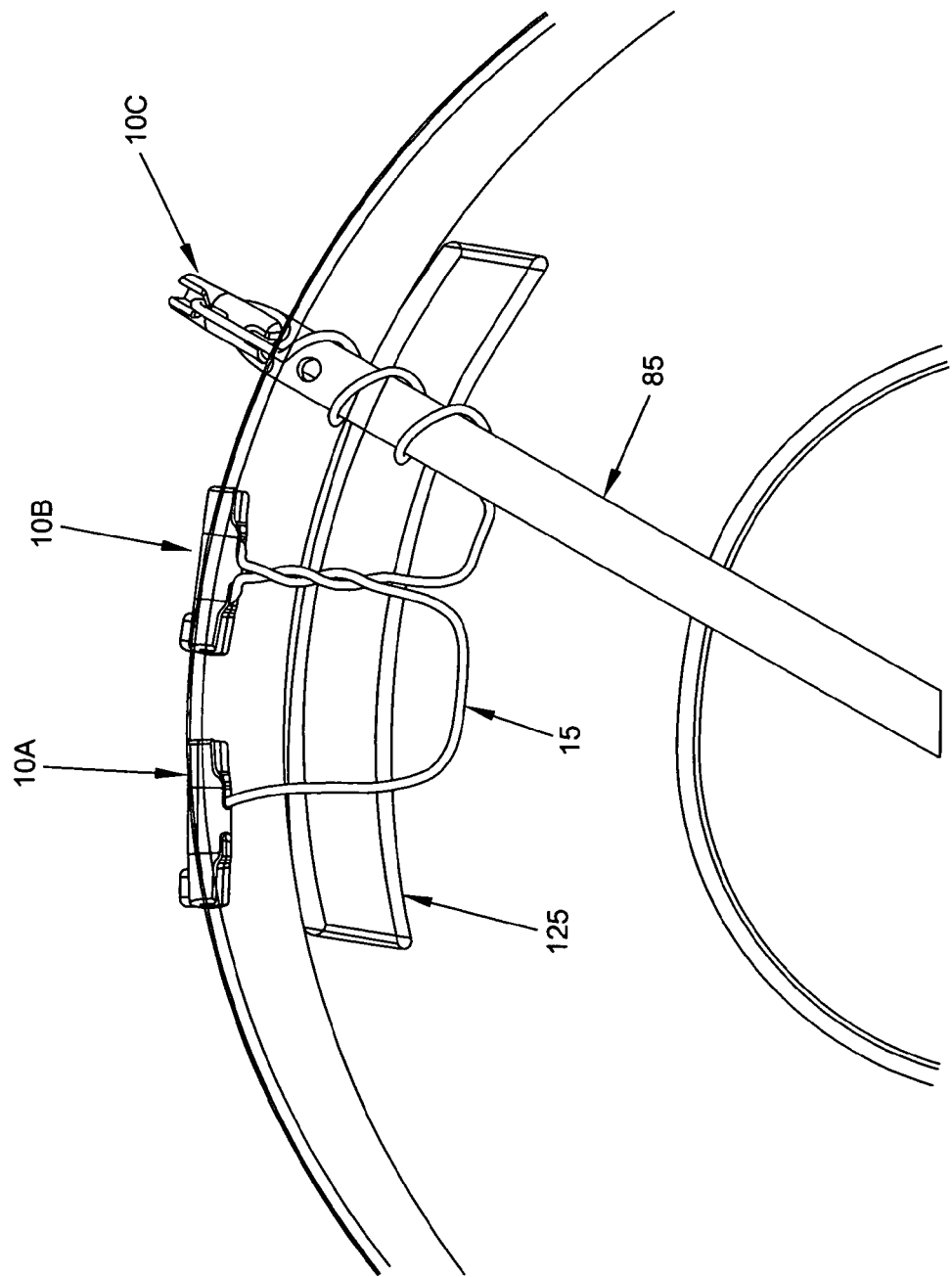
Figure 22:
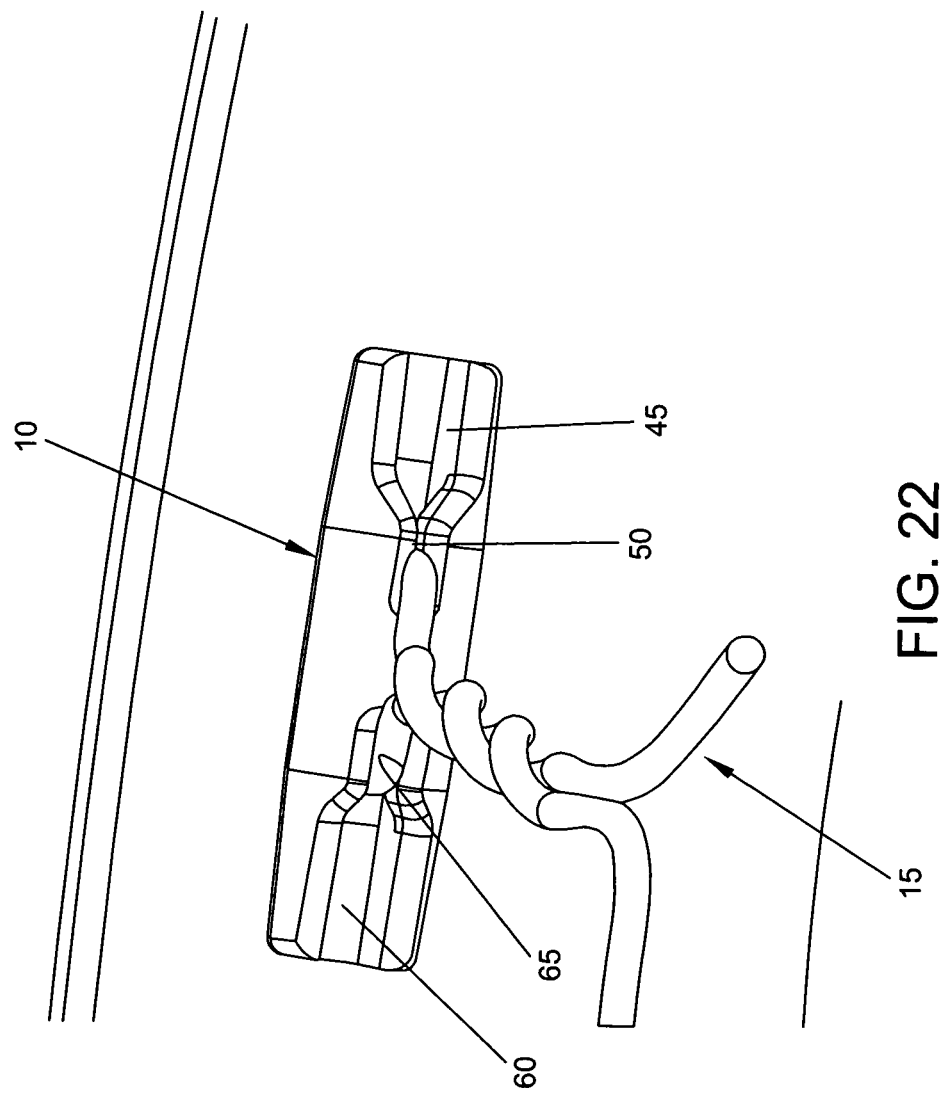

However, it has also been discovered that, to the extent that it is desired to provide even greater holding strength to the system, suture 15 can be twisted on itself during deployment so as to achieve holding strength of up to 75 Newtons without requiring any change to the diameter of narrow section 50 of distal slot 40. More particularly, and looking now at FIGS. 20-22, sharp point 95 of inserter 20 is advanced into meniscus 130, across tear 125, and then out the far side of meniscus 130. Then, with suture 15 in a relaxed condition, a first anchor 10A is ejected from lumen 90 of inserter 20 so that the first anchor 10A sits on the far side of the meniscus. As this occurs, first anchor 10A will tend to turn as it exits lumen 90, but suture 15 will tend to stay in wide section 45 of distal slot 40 and not enter narrow section 50 of distal slot 40. Thus, at this point, suture 15 is still relatively free to slide relative to first anchor 10A. With suture 15 still in a relaxed condition, inserter 20 is then withdrawn from meniscus 130, moved laterally, re-inserted across tear 125 and passed out the far side of meniscus 130. Then elongated shaft 85 of inserter 20 is rotated so as to wrap the suture around the inserter. By way of example but not limitation, inserter 20 may be rotated three revolutions. As this occurs, there can be some gathering of the slack between first anchor 10A and inserter 20 and/or there can be some pay out of the suture stored inside the inserter. At this point, a second anchor 10B is ejected from lumen 90 of inserter 20 so that second anchor 10B sits on the far side of the meniscus. Inserter 20 is then withdrawn back through the meniscus. Then the suture is tensioned (e.g., with tension wheel 120) so that (i) the suture between anchors 10A and 10B is reduced, so as to close the tear in the meniscus, (ii) the winding in the suture is pulled taut, and (iii) the suture is forced into narrow section 50 of distal slot 40 and narrow section 65 or proximal slot 55. As a result, this approach provides both the aforementioned cleating action provided by capturing the suture within narrow section 50 of distal slot 40, and also a supplemental securing action provided by the suture which has been wound on itself. In practice, it has been found that this dual effect provides approximately 75 Newtons of holding strength.

Thereafter, additional anchors may be provided as needed so as to close the tear.

FIGS. 23 and 24 show an alternative construction for anchor 10. More particularly, with the construction shown in FIGS. 23 and 24, the distal and proximal portion of elongated body 25 are cut back on the "top" of the anchor, and recess 75 is elongated relative to distal slot 40 and proximal slot 55.

Thus, the present invention provides a meniscal repair system which comprises a plurality of anchors that ride over a single suture strand, which can be singly deployed within the body, with each single anchor acting as an independent fixation point for the suture strand. The ability to lock the suture within each anchor (such as with the cleating feature provided for each anchor) provides the ability for each anchor to act as an independent fixation point for the suture strand. Furthermore, these independent fixation points allow the suture, running from one anchor to the next anchor, to act as an independent suture stitch. Additionally, the entire contiguous repair construct consists of multiple independent suture stitches extending between multiple adjacent anchors, with the construct such that if one or more stitches are damaged or become loose or disengaged from an anchor, the other suture stitches are unaffected. Also, the ability to individually tighten each suture stitch (i.e., the suture strand extending between adjacent anchors) by drawing the suture through the deployed anchor's locking feature permits the desired suture tension to be achieved.

The present invention provides the ability to position variable suture patterns across the torn meniscus in a contiguous fashion. Significantly, the repairing construct can have more than two points of fixation to the meniscus using a single strand of suture, and does not require any suture tying.

Also, the present invention provides the ability to remove an anchor from a deployed suture construct without disrupting previously-deployed anchors. This would be accomplished by sliding the dislodged implant along the suture strand outside of the body and breaking or cutting the implant without damaging the suture. The user can then continue to deliver subsequent implants from the same device to complete the repair.

And the present invention provides the ability to cut the suture strand after two or more implants have been deployed into the body, and then secure the deployed suture strand to the leading anchor in the inserter (e.g., by knotting) so that the user can continue to deploy subsequent unused anchors still residing within the inserter as part of the repair construct.

The present invention provides a gating mechanism for singly deploying each anchor from the inserter, e.g., fin 80, slot 105 and projection 106.

Furthermore, the present invention provides an approach for wrapping or twisting the suture around the inserter prior to ejection of an anchor so as to form a suture loop around the suture emanating from the anchor, so that subsequent tightening of the suture through the anchor draws the wrapped suture loop towards the anchor and further secures the suture to the anchor.

Modifications

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A system comprising:
 a suture; and
 at least one anchor, said anchor comprising: an elongated cylindrical body having a distal end, a proximal end, a first side, a second side diametrically opposed to the first side, a longitudinal axis extending between the distal end and the proximal end, and a cylindrical outer surface radially offset from the longitudinal axis, the distal end having on the first side of the body a distal slot opening on the cylindrical outer surface of said body and extending from the distal end of said body proximally along the longitudinal axis of said body, and the proximal end having on the first side of the body a proximal slot opening on the cylindrical outer surface of said body and extending from the proximal end of said body distally along the longitudinal axis of said body, the distal slot and the proximal slot extending only on the first side of the body;
 the distal slot comprising a wide section and a narrow section, wherein the wide section is provided with a width such that said suture is slidably accommodated therein, and the narrow section is provided with a width such that said suture is bound therein, and further wherein said wide section is disposed distally of said narrow section;
 wherein said body is adapted such that said suture is initially disposed within said wide section of the distal slot of said anchor and the proximal slot of said anchor, such that said suture is slidable relative to said anchor; and
 further wherein said body is adapted such that said suture is thereafter disposed within the narrow section of the distal slot of the anchor in order to bind said suture to said body.

2. A system according to claim 1 comprising a plurality of anchors, and further wherein, for each of said anchors, said suture is initially disposed within said wide section of the distal slot and the proximal slot of said anchor, such that said suture is slidable relative to said plurality of anchors.

3. A system according to claim 1 comprising a plurality of said anchors, and further wherein, for each of said anchors, the suture is thereafter disposed within said narrow section of the distal slot, whereby to bind the suture to the plurality of said anchors.

4. A system according to claim 3 wherein tension in the suture between each pair of said anchors is independent of tension in the suture between every other pair of said anchors.

5. A system according to claim 1 further comprising an inserter,
wherein said inserter comprises a hollow elongated shaft provided with a sharp point disposed eccentric to a longitudinal axis of said hollow elongated shaft;
and further wherein said suture and said at least one anchor are disposed within a lumen of said hollow elongated shaft.

6. A system according to claim 5 wherein said inserter further comprises a drive shaft movably disposed within the lumen of said hollow elongated shaft, whereby to selectively eject said at least one anchor from the lumen of said hollow elongated shaft.

7. A system according to claim 6 wherein said inserter further comprises an element for engaging said at least one anchor moving through said hollow elongated shaft and retarding movement of said at least one anchor through the lumen of said hollow elongated shaft.

8. A system according to claim 7 wherein said at least one anchor comprises a fin, wherein said hollow elongated shaft is provided with a slot for receiving said fin, and further wherein said element comprises a projection into the slot.

9. A system according to claim 5 wherein said inserter comprises a tensioning element for tensioning said suture.

10. A system according to claim 1 wherein the elongated body further comprises a recess, and further wherein the recess is diametrically opposed to the distal slot and the proximal slot.

11. An anchor for securing suture to tissue, the anchor comprising:
an elongated cylindrically shaped body having a distal end, a proximal end, a longitudinal axis extending between the distal end and the proximal end and a cylindrical outer surface radially offset from the longitudinal axis, said body being adapted for disposition in a lumen of a delivery needle for repair of tissue, said body comprising:
a first side having a distal slot opening on the cylindrical outer surface of the body and extending from the distal end of said body along the longitudinal axis toward the proximal end of said body, the distal slot extending only on the first side of the body;
the distal slot comprising a first section extending from adjacent the distal end of said body and a second section extending from the distal slot first section toward the proximal end of said body and terminating in said body;
the distal slot second section being narrower than the distal slot first section;
said first side having a proximal slot opening on the cylindrical outer surface of the body and extending from the proximal end of said body along the longitudinal axis toward the distal end of said body and terminating in said body in alignment with and removed from an end of the distal slot, the proximal slot extending only on the first side of the body;
the proximal slot comprising a first section extending from the proximal end of said body and a second section extending from the proximal slot first section and towards the distal slot and in alignment therewith; and
a recess in a second side of the body diametrically opposed from the first side of said body and extending from a point removed from the distal end of said body to a point removed from the proximal end of said body, said recess being in communication with the distal slot and the proximal slot;
the anchor being adapted to receive a suture at the proximal slot, which suture is adapted to extend through the body and out the distal slot first section, and is selectively retained in the distal slot second section by a widthwise narrowness of the distal slot second section relative to a diameter of the suture.

12. The anchor in accordance with claim 11 wherein the proximal slot first section is of greater width than the proximal slot second section.

13. An anchor according to claim 12 wherein the proximal slot second section has a width such that the suture is slidably accommodated therein.

14. An anchor according to claim 11 wherein said recess is diametrically opposed to said distal slot and the proximal slot.

15. An anchor according to claim 14 wherein said recess is in communication with the first section of the distal slot, the second section of the distal slot, and the proximal slot.

16. An anchor according to claim 11 wherein the elongated body is non-tubular.

17. An anchor according to claim 11 wherein the elongated body further comprises a fin disposed thereon and extending lengthwise of said body from said proximal end to proximate said recess.

18. An anchor according to claim 17 wherein said fin is aligned with said recess.

19. The anchor in accordance with claim 11 wherein the distal slot and the proximal slot are in lengthwise alignment and the ends of the distal slot and the proximal slot are spaced from each other by a portion of said body.

20. The anchor in accordance with claim 19 and further comprising a fin disposed on said second side of said body at said proximal end and extending to proximate said recess.

21. The anchor in accordance with claim 20 wherein said fin is configured and sized to slidably move along a groove in a tool shaft.

22. The anchor in accordance with claim 11 wherein a wall portion of said body is disposed between said distal slot second portion and said proximal slot second portion and defines an internal wall of said body, and the suture is adapted to extend along the internal wall between said distal slot second portion and said proximal slot second portion.

* * * * *